United States Patent
Ward

(12) 
(10) Patent No.: US 6,399,368 B1
(45) Date of Patent: Jun. 4, 2002

(54) **SECRETION OF T CELL RECEPTOR FRAGMENTS FROM RECOMBINANT *ESCHERICHIA COLI* CELLS**

(75) Inventor: Elizabeth S. Ward, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 08/353,940

(22) Filed: Dec. 9, 1994

Related U.S. Application Data

(63) Continuation-in-part of application No. 07/873,930, filed on Apr. 24, 1992, now abandoned, which is a continuation-in-part of application No. 07/822,302, filed on Jan. 17, 1992, now abandoned.

(51) Int. Cl.$^7$ .............................................. C12N 15/13
(52) U.S. Cl. ...................... 435/320.1; 435/6; 435/71.1; 435/170; 435/252.8; 435/252.3; 536/24.1; 536/25.3
(58) Field of Search ................. 536/25.3, 24.1; 435/6, 71.1, 172.3, 252.3, 270, 317.1, 320.1, 253.6, 170, 803, 252.8

(56) References Cited

U.S. PATENT DOCUMENTS

| | | | |
|---|---|---|---|
| 4,554,101 A | 11/1985 | Hopp | |
| 4,970,296 A | * 11/1990 | Saito et al. | ................. 530/323 |
| 5,185,250 A | 2/1993 | Brenner et al. | ............ 435/69.3 |

FOREIGN PATENT DOCUMENTS

| | | |
|---|---|---|
| EP | A O 368 684 | 5/1990 |
| WO | WO91/08298 | 6/1991 |
| WO | WO92/01787 | 2/1992 |

OTHER PUBLICATIONS

Korman et al., J. Exp. Med, vol. 168, pp. 1021–1040, 1988.*
Iwamoto et al, J. Exp. Med, vol. 165, pp. 591–600, 1987.*
Arden et al, Nature, vol. 316, pp. 783–787, 1985.*
Chou et al, Proc. Natl. Acad. Sci, U.S.A., vol. 84, 1987, pp 1992–1996.*
Becker et al, Nature, vol. 317, pp. 430–434, 1985.*
Behlke et al, Science, vol. 229, pp. 566–570, 1985.*
Davis et al, Nature, vol. 334, pp. 395–401, 1988.*
Yanagi et al, Nature, vol. 308 pp. 145–148, 1984.*
Loh et al, Science, vol. 243, pp 217–243, 1989.*
Roth et al, Science, vol. 241, pp. 1354–1358, 1988.*
Takihara et al, Proc. Natl. Acad. Sci. USA, vol. 85, pp 6097–6101, 1988.*
Hedrick et al, Nature, vol. 308, 1984, pp 153–158.*
Adelman, J.P., Hayflick, J.S., Vasser, M. and Seeburg, P.H., "In Vitro Deletional Mutagenesis for Bacterial Production of the 20,000–Dalton form of Human Pituitary Growth Hormone," *DNA* 2(3):183–193 (1983).

Better, M., Chang, C.P., Robinson, R.R. and Horwitz, A.H., "*Escherichia coli* Secretion of an Active Chimeric Antibody Fragment," *Science*, 240:1041–1043 (1988).
Bhat, T.N., Bentley, G.A., Fischmann, T.O., Boulot, G. and Poljak, R.J., "Small Rearrangements in Structures of Fv and Fab Fragments of Antibody D1.3 on Antigen Binding," *Nature*, 347:483–485 (1990).
Borst, J., et al., "A T–cell Receptor γ/CD3 Complex Found on Cloned Functional Lymphocytes," *Nature*, 325:683–688 (1987).
Brenner, M.B., et al., "Identification of a Putative Second T–cell Receptor," *Nature*, 322:145–149 (1986).
Carter, P.J., Bedouelle, H., Winter, G., "Improved Oligonucleotide Site–directed Mutagenesis Using M13 Vectors," *Nucleic Acids Res.*, 13:4431–4443 (1985).
Chothia, C., Boswell, D.R. and Lesk, A.M., "The Outline Structure of the T–cell αβ Receptor," *EMBO J.*, 7:3745–3755 (1986).
Crea, R., et al., "Chemical Synthesis of Genes for Human Insulin," *Proc. Natl. Acad. Sci. USA*, 75(12):5765–5769 (1978).
Devaux, B., Bjorkman, P.J., Stevenson, C., Greif, W., Elliot, J.F., Sagerström, C., Clayberger, C., Krensky, A.M. and Davis, M.M., "Generation of Monoclonal Antibodies Against Soluble Human T Cell Receptor Polypeptides," *Eur. J. Immunol.*, 21:2111–2119 (1991).
Evan, G.I., Lewis, G.K., Ramsay, G. and Bishop, J.M., "Isolation of Monoclonal Antibodies Specific for Human 2c–myc Proto–Oncogene Product," *Mol. Cell. Biol.*, 5(12):3610–3616 (1985).
Fleury, S., Lamarre, D., Meloche, S., Ryu, S–E., Cantin, C., Hendrickson, W.A. and Sekaly, R–P., "Mutational Analysis of the Interaction Between CD4 and Class II MHC: Class II Antigens Contact CD4 on a Surface Opposite the gp120–Binding Site," *Cell*, 66:1037–1049 (1991).
Gascoigne, N.R.J., "Transport and Secretion of Truncated T Cell Receptor β–Chain Occurs in the Absence of Association with CD3," *J. Biol. Chem.*, 265(6):9296–9301 (1990).
Gascoigne, N.R.J., et al., "Secretion of a Chimeric T–Cell Receptor–Immunoglobulin Protein," *Proc. Natl. Acad. Sci. USA*, 84:2936–2940 (1987).

(List continued on next page.)

Primary Examiner—James Housel
(74) Attorney, Agent, or Firm—Fulbright & Jaworski, LLP

(57) ABSTRACT

Variable domain murine T-cell receptor genes have been isolated and used to construct cloning and expression vectors. $V_\alpha$, $V_\beta$ and single chain $V_\alpha$–$V_\beta$ fragments have been expressed as secreted domains in *Escherichia coli* using the vectors. The domains are secreted into the culture supernatant in milligram quantities. The single domains and the single chain T-cell receptors are folded into β-pleated sheet structures similar to those of immunoglobulin variable domains. The secreted fragments may be useful for immunization to generate anti-clonotypic antibodies, in vaccination or for high resolution structural studies. The genes encoding these domains may also serve as templates for in vitro mutagenesis and improvement of affinities of the TCR fragments for their interaction with cognate peptide-MHC complexes.

26 Claims, 12 Drawing Sheets

OTHER PUBLICATIONS

Grégoire, C., Rebai, N., Schweisguth, F., Necker, A., Mazza, G., Auphan, N., Millward, A., Schmitt–Verhulst, A–M. and Malissen, B., "Engineered Secreted T–Cell Receptor αβ Heterodimers," *Proc. Natl. Acad. Sci. USA*, 88:8077–8081 (1991).

Harding, C.V. and Unanue, E.R., "Quantitation of Antigen–Presenting Cell MHC Class II/Peptide complexes Necessary for T–Cell Stimulation," *Nature*, 346:574–576 (1990).

Howell, M.D., Winters, S.T., Olee, T., Powell, H.C., Carlo, D.J., Brostoff, S.W., "Vaccination Against Experimental Allergic Encephalomyelitis with T Cell Receptor Peptides," *Science*, 246:668–670 (1989).

Huse, W.D., et al., "Generation of a Large Combinatorial Library of the Immunoglobulin Repertoire in Phage Lambda," *Science*, 246:1275–1281, (1989).

Huston, J.S., Levinson, D., Mudgett–Hunter, M., Tai, M–S, Novotny, J., Margolies, M.N., Ridge, R.J., Bruccoleri, R.E., Haber, E., Crea, R. and Oppermann, H., "Protein Engineering of Antibody Binding Sites: Recovery of Specific Activity in an Anti–Digoxin Single–Chain Fv Analogue Produced in *Escherichia coli*," *Proc. Natl. Acad. Sci. USA*, 85:5879–5883 (1988).

Johnson, W.C., "Protein Secondary Structure and Circular Dichroism: A Practical Guide," *Proteins*, 7:205–214 (1990).

Kappler, J.W., Staerz, U., White, J. and Marrack, P.C., "Self–Tolerance Eliminates T Cells Specific for Mls–Modified Products of the Major Histocompatibility Complex," *Nature*, 332:35–40 (1988).

Kyte, J., and Doolittle, R.F., "A Simple Method for Displaying the Hydropathic Character of a Protein," *J. Mol. Biol.*, 157:105–132 (1982).

Lin, A.Y., Devaux, B., Green, A., Sagerström, C. Elliott, J.F. and Davis, M.M., "Expression of T Cell Antigen Receptor Heterodimers in a Lipid–Linked Form," *Science*, 249:677–679 (1990).

McCafferty, J., Griffiths, A.D., Winter, G., and Chiswell, D.J., "Phage Antibodies: Filamentous Phage Displaying Antibody Variable Domains," *Nature*, 348:552–554 (1990).

Mariuzza, R.A. and Winter, G.P., "Secretion of a Homodimeric VαCk T Cell Receptor–Immunoglobulin Chimeric Protein," *J. Biol. Chem.*, 264(13):7310–7316 (1989).

Messing, J., Crea, R., and Seeburg, P.H., "A System for Shotgun DNA Sequencing," *Nucleic Acids Research*, 9(2):309–321 (1981).

Novotny, J., Tonegawa, S., Saito, H., Kranz, D.M. and Eisen, H.N., "Secondary, Tertiary, and Quaternary Structure of T–Cell–Specific Immunoglobulin–Like Polypeptide Chains," *Proc. Natl. Acad. Sci. USA*, 83:742–746 (1986).

Novotny, J., Ganju, R., Smiley, S.T., Hussey, R.E., Luther, M.A., Recny, M.A., Siliciano, R.F., and Reinherz, E.L., "A Soluble, Single–Chain T–Cell Receptor Fragment Endowed with Antigen–Combining Properties," *Proc. Natl. Acad. Sci. USA*, 88:8646–8650 (1991).

Offner, H., Hashim, G.A., Vandenbark, A.A., "T Cell Receptor Peptide Therapy Triggers Autoregulation of Experimental Encephalomyelitis," *Science*, 251:430–432 (1991).

Rüther, U., Koenen, M., Otto, K. and Müller–Hill, B., "pUR222, a Vector for Cloning and Rapid Chemical Sequencing of DNA," *Nucl. Acids Res.*, 9(16):4087–4098 (1981).

Saiki, R.K., Gelfand, D.H., Stoffel, S., Scharf, S.J., Higuchi, R., Horn, G.T., Mullis, K.V. and Erlich, H.A., "Primer–Directed Enzymatic Amplification of DNA with a Thermostable DNA Polymerase," *Science* 239:487–491 (1988).

Sleckman, B.P., Peterson, A., Jones, W.K., Foran, J.A., Greenstein, J.L., Seed, B. and Burakoff, S.J., "Expression an Function of CD4 in a Murine T–Cell Hybridoma," *Nature*, 328:351–353 (1987).

Skerra, A. and Plückthun, A., Assembly of a Functional Immunoglobulin $F_V$ Fragment in *Escherichia coli*, *Science*, 240:1038–1041 (1988).

Takagi, H., Morinaga, Y., Tsuchiya, M., Ikemura, H. and Inouye, M., "Control of Folding of Proteins Secreted by a High Expression Secretion Vector, pIN–III–ompA: 16–Fold Increase in Production of Active Subtilisin E in *Escherichia coli*," *Bio/Technol.*, 6:948–950 (1988).

Toki, J., et al., "Analyses of T–Cell Differentiation from Hemopoietic Stem Cells in the $G_0$ Phase by an in vitro Method," *Proc. Natl. Acad. Sci. USA*, 88:7549–7551 (1991).

Towbin, H., Stachelin, T. and Gordon, J., "Electrophoretic Transfer of Proteins from Polyacrylamide Gels to Nitrocellulose Sheets: Procedure and Some Applications," *Proc. Natl. Acad. Sci.*, 76(9):4350–4354 (1979).

Vandenbark, A.A., Hashim, G. and Offner, H., Immunization with a Synthetic T–Cell Receptor V–Region Peptide Protects Against Experimental Autoimmune Encephalomyelitis, *Nature*, 331:541–544 (1989).

Vieira, J. and Messing, J., "Production of Single–Stranded Plasmid DNA," *Methods in Enzymology*, 153:3–11 (1987).

Ward, E.S., Güssow, D., Griffiths, A.D., Jones, P.T. and Winter, G., "Binding Activities of a Repertoire of Single Immunoglobulin ?Variable Domains Secreted from *Escherichia coli*," *Nature*, 341:544–546 (1989).

Ward, E.S., "Expression and Secretion of T–Cell Receptor Vα and Vα Domains using *Escherichia coli* as a Host," *Scand. J. Immunol.*, 34:215–220 (1991).

Ward, E.S., "Secretion of T–Cell Receptor Fragments from Recombinant *Escherichia coli* Cells," *J. Mol. Biol.*, 224:2885–890 (1992).

Whitlow, M. and Filpula, D., "Single–Chain FV Proteins and Their Fusion Proteins," *Methods: A Companion to Methods in Enzymology*, 2(2):97–105 (1991).

Wraith, D.C., Smilek, D.E., Mitchell, D.J., Steinman, L. and McDevitt, H.O., "Antigen Recognition in Autoimmune Encephalomyelitis and the Potential for Peptide–Mediated Immunotherapy," *Cell*, 59, 247–255 (1989).

Dembić et al., "Transfer of Specificity by Murine α and β T–cell Receptor Genes," *Nature*, 320:232–238, 1986.

Gray and Goeddel, "Cloning and Expression of Murine Immune Interferon cDNA," *Proc. Natl. Acad. Sci. USA*, 80:5842–5846, 1983.

Kurucz et al., "A Bacterially Expressed Single–chain Fv Construct from the 2B4 T–cell Receptor," *Proc. Natl. Acad. Sci. USA*, 90:3830–3834, 1993.

Saito and Germain, "Predictable Acquisition of a New MHC Recognition Specificty Following Expression of a Transfected T–cell Receptor β–chain Gene," *Nature*, 329:256–259, 1987.

Acha–Orbea, Hans et al., "Limited Heterogeneity of T Cell Receptors from Lymphocytes Mediating Autoimmune Encephalomyelitis Allows Specific Immune Intervention" (1988) *Cell* 54:263–273.

Soo Hoo, W.F. et al., "Characterization of a Single–Chain T–cell Receptor Expressed in *Escherichia coli*" (1992) *Proc. Natl. Acad. Sci. USA* 89:4759–4763.

* cited by examiner

```
1   /   1                                      31   /   11
GAC TCA GTG ACT CAG ACG GAA GGT CAA GTG        GCC CTC TCA GAA GAG GAC TTT CTT ACG ATA
asp ser val thr gln thr glu gly gln val        ala leu ser glu glu asp phe leu thr ile
61  /   21                                     91   /   31
CAC TGC AAC TAC TCA GCC TCA GGG TAC CCA        GCT CTG TTC TGG TAT GTG CAG TAT CCC GGA
his cys asn tyr ser ala ser gly tyr pro        ala leu phe trp tyr val gln tyr pro gly
121 /   41                                     151  /   51
GAA GGG CCA CAG TTC CTC TTT AGA GCC TCA        AGG GAC AAA GAG AAA GGA AGC AGC AGA GGG
glu gly pro gln phe leu phe arg ala ser        arg asp lys glu lys gly ser ser arg gly
181 /   61                                     211  /   71
TTT GAA GCC ACA TAC AAT AAA GAA GCC ACC        TCC TTC CAC TTG CAG AAA GCC TCA GTG CAA
phe glu ala thr tyr asn lys glu ala thr        ser phe his leu gln lys ala ser val gln
241 /   81                                     271  /   91
GAG TCA GAC TCG GCT GTG TAC TAC TGC GCT        CTG AGT GAA AAC TAT GGA AAT GAG AAA ATA
glu ser asp ser ala val tyr tyr cys ala        leu ser glu asn tyr gly asn glu lys ile
301 /   101                                    331  /   111
ACT TTT GGG GCT GGA ACC AAA CTC ACC ATT        AAA CCG GGT GGA GGC GGT TCA GGC GGA GGT
thr phe gly ala gly thr lys leu thr ile        lys pro gly gly gly gly ser gly gly gly
361 /   121                                    391  /   131
GGA TCC GGC GGT GGC GGA TCG GAG GCT GCA        GTC ACC CAA AGC CCA AGA AAC AAG GTG GCA
gly ser gly gly gly gly ser glu ala ala        val thr gln ser pro arg asn lys val ala
421 /   141                                    451  /   151
GTA ACA GGA GGA AAG GTG ACA TTG AGC TGT        AAT CAG ACT AAT AAC CAC AAC AAC ATG TAC
val thr gly gly lys val thr leu ser cys        asn gln thr asn asn his asn asn met tyr
481 /   161                                    511  /   171
TGG TAT CGG CAG GAC ACG GGG CAT GGG CTG        AGG CTG ATC CAT TAT TCA TAT GGT GCT GGC
trp tyr arg gln asp thr gly his gly leu        arg leu ile his tyr ser tyr gly ala gly
541 /   181                                    571  /   191
AGC ACT GAG AAA GGA GAT ATC CCT GAT GGA        TAC AAG GCC TCC AGA CCA AGC CAA GAG AAC
ser thr glu lys gly asp ile pro asp gly        tyr lys ala ser arg pro ser gln glu asn
601 /   201                                    631  /   211
TTC TCC CTC ATT CTG GAG TTG GCT ACC CCC        TCT CAG ACA TCA GTG TAC TTC TGT GCC AGC
phe ser leu ile leu glu leu ala thr pro        ser gln thr ser val tyr phe cys ala ser
661 /   221                                    691  /   231
GGT GAT GCG TCG GGA GCA GAA ACG CTG TAT        TTT GGC TCA GGA ACC AGA CTG ACT GTT CTG
gly asp ala ser gly ala glu thr leu tyr        phe gly ser gly thr arg leu thr val leu
721 /   241
GTC ACC CAT CAC CAT CAC CAT CAC TAA
val thr his his his his his his OCH
```

FIGURE 9

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH:     363 base pairs
      (B) TYPE:       nucleic acid
      (C) STRANDEDNESS: sin gle
      (D) TOPOLOGY:   linear (xi) SEQUENCE DESCRIPTION: SEQ ID NO: 1:

```
GACTCAGTGA CTCAGACGGA AGGTCAAGTG GCCCTCTCAG AAGAGGACTT T CTTACGATA     60

CACTGCAACT ACTCAGCCTC AGGGTACCCA GCTCTGTTCT GGTATGTGCA G TATCCCGGA    120

GAAGGGCCAC AGTTCCTCTT TAGAGCCTCA AGGGACAAAG AGAAAGGAAG C AGCAGAGGG    180
```

TTTGAAGCCA CATACAATAA AGAAGCCACC TCCTTCCACT TGCAGAAAGC C TCAGTGCAA    240

GAGTCAGACT CGGCTGTGTA CTACTGCGCT CTGAGTGAAA ACTATGGAAA T GAGAAAATA    300

ACTTTTGGGG CTGGAACCAA ACTCACCATT AAACCGGTCA CCCATCACCA T CACCATCAC    360

TAA    363

(2) INFORMATION FOR SEQ ID NO: 2:

(i) SEQUENCE CHARACTERISTICS:
        (A) LENGTH:        120 amino acid residues
        (B) TYPE:          amino acid
        (C) STRANDEDNESS:  sin gle
        (D) TOPOLOGY:      linear (xi) SEQUENCE DESCRIPTION: SEQ ID NO : 2:

Asp Ser Val Thr Gln Thr Glu Gly Gln Val A la Leu Ser Glu Glu Asp
 1               5                  10                  15

Phe Leu Thr Ile His Cys Asn Tyr Ser Ala S er Gly Tyr Pro Ala Leu
             20                  25                  30

Phe Trp Tyr Val Gln Tyr Pro Gly Glu Gly P ro Gln Phe Leu Phe Arg
         35                  40                  45

Ala Ser Arg Asp Lys Glu Lys Gly Ser Ser A rg Gly Phe Glu Ala Thr
     50                  55                  60

Tyr Asn Lys Glu Ala Thr Ser Phe His Leu G ln Lys Ala Ser Val Gln
 65                  70                  75                  80

Glu Ser Asp Ser Ala Val Tyr Tyr Cys Ala L eu Ser Glu Asn Tyr Gly
                 85                  90                  95

Asn Glu Lys Ile Thr Phe Gly Ala Gly Thr L ys Leu Thr Ile Lys Pro
             100                 105                 110

Val Thr His His His His His His
         115                 120

(2) INFORMATION FOR SEQ ID NO: 3:

(i) SEQUENCE CHARACTERISTICS:
        (A) LENGTH:        366 base pairs
        (B) TYPE:          nucleic acid
        (C) STRANDEDNESS:  sin gle
        (D) TOPOLOGY:      linear (xi) SEQUENCE DESCRIPTION: SEQ ID NO : 3:

GAGGCTGCAG TCACCCAAAG CCCAAGAAAC AAGGTGGCAG TAACAGGAGG A AAGGTGACA    60

TTGAGCTGTA ATCAGACTAA TAACCACAAC AACATGTACT GGTATCGGCA G GACACGGGG    120

CATGGGCTGA GGCTGATCCA TTATTCATAT GGTGCTGGCA GCACTGAGAA A GGAGATATC    180

CCTGATGGAT ACAAGGCCTC CAGACCAAGC CAAGAGAACT TCTCCCTCAT T CTGGAGTTG    240

GCTACCCCCT CTCAGACATC AGTGTACTTC TGTGCCAGCG GTGATGCGTC G GGAGCAGAA    300

ACGCTGTATT TGGCTCAGG AACCAGACTG ACTGTTCTGG TCACCCATCA C CATCACCAT    360

CACTAA    366

(2) INFORMATION FOR SEQ ID NO: 4:

(i) SEQUENCE CHARACTERISTICS:
        (A) LENGTH:        121 amino acid residues
        (B) TYPE:          amino acid
        (C) STRANDEDNESS:  sin gle
        (D) TOPOLOGY:      linear (xi) SEQUENCE DESCRIPTION: SEQ ID NO : 4:

```
Glu Ala Ala Val Thr Gln Ser Pro Arg Asn Lys Val Ala Val Thr Gly
 1               5                  10                  15

Gly Lys Val Thr Leu Ser Cys Asn Gln Thr Asn Asn His Asn Asn Met
                20                  25                  30

Tyr Trp Tyr Arg Gln Asp Thr Gly His Gly Leu Arg Leu Ile His Tyr
            35                  40                  45

Ser Tyr Gly Ala Gly Ser Thr Glu Lys Gly Asp Ile Pro Asp Gly Tyr
        50                  55                  60

Lys Ala Ser Arg Pro Ser Gln Glu Asn Phe Ser Leu Ile Leu Glu Leu
65                  70                  75                  80

Ala Thr Pro Ser Gln Thr Ser Val Tyr Phe Cys Ala Ser Gly Asp Ala
                85                  90                  95

Ser Gly Ala Glu Thr Leu Tyr Phe Gly Ser Gly Thr Arg Leu Thr Val
            100                 105                 110

Leu Val Thr His His His His His His
            115                 120
```

(2) INFORMATION FOR SEQ ID NO: 5:

(i) SEQUENCE CHARACTERISTICS:
        (A) LENGTH:      753 base pairs
        (B) TYPE:        nucleic acid
        (C) STRANDEDNESS: single
        (D) TOPOLOGY:    linear (xi) SEQUENCE DESCRIPTION: SEQ ID NO : 5:

```
GACTCAGTGA CTCAGACGGA AGGTCAAGTG GCCCTCTCAG AAGAGGACTT T CTTACGATA    60
CACTGCAACT ACTCAGCCTC AGGGTACCCA GCTCTGTTCT GGTATGTGCA G TATCCCGGA   120
GAAGGGCCAC AGTTCCTCTT TAGAGCCTCA AGGGACAAAG AGAAGGAAG C AGCAGAGGG    180
TTTGAAGCCA CATACAATAA AGAAGCCACC TCCTTCCACT TGCAGAAAGC C TCAGTGCAA   240
GAGTCAGACT CGGCTGTGTA CTACTGCGCT CTGAGTGAAA ACTATGGAAA T GAGAAAATA   300
ACTTTTGGGG CTGGAACCAA ACTCACCATT AAACCGGTCA CCGGTGGAGG C GGTTCAGGC   360
GGAGGTGGCT CTGGCGGTGG CGGATCGGAG GCTGCAGTCA CCCAAAGCCC A AGAAACAAG   420
GTGGCAGTAAC AGGAGGAAA GGTGACATTG AGCTGTAATC AGACTAATAA C CACAACAAC   480
ATGTACTGGTA TCGGCAGGA CACGGGGCAT GGGCTGAGGC TGATCCATTA T TCATATGGT   540
GCTGGCAGCAC TGAGAAAGG AGATATCCCT GATGGATACA AGGCCTCCAG A CCAAGCCAA   600
GAGAACTTCTC CCTCATTCT GGAGTTGGCT ACCCCTCTC AGACATCAGT G TACTTCTGT   660
GCCAGCGGTGA TGCGTCGGG AGCAGAAACG CTGTATTTTG GCTCAGGAAC C AGACTGACT   720
GTTCTGGTCAC CCATCACCA TCACCATCAC TAA                                753
```

(2) INFORMATION FOR SEQ ID NO: 6:

(i) SEQUENCE CHARACTERISTICS:
        (A) LENGTH:      250 amino acid residues
        (B) TYPE:        amino acid
        (C) STRANDEDNESS: single
        (D) TOPOLOGY:    linear (xi) SEQUENCE DESCRIPTION: SEQ ID NO : 6:

```
Asp Ser Val Thr Gln Thr Glu Gly Gln Val Ala Leu Ser Glu Glu Asp
 1               5                  10                  15

Phe Leu Thr Ile His Cys Asn Tyr Ser Ala Ser Gly Tyr Pro Ala Leu
                20                  25                  30
```

```
Phe Trp Tyr Val Gln Tyr Pro Gly Glu Gly P ro Gln Phe Leu Phe Arg
            35                  40                  45

Ala Ser Arg Asp Lys Glu Lys Gly Ser Ser A rg Gly Phe Glu Ala Thr
        50                  55                  60

Tyr Asn Lys Glu Ala Thr Ser Phe His Leu G ln Lys Ala Ser Val Gln
65                  70                  75                  80

Glu Ser Asp Ser Ala Val Tyr Tyr Cys Ala L eu Ser Glu Asn Tyr Gly
                85                  90                  95

Asn Glu Lys Ile Thr Phe Gly Ala Gly Thr L ys Leu Thr Ile Lys Pro
            100                 105                 110

Val Thr Gly Gly Gly Ser Gly Gly Gly G ly Ser Gly Gly Gly Gly
        115                 120                 125

Ser Glu Ala Ala Val Thr Gln Ser Pro Arg A sn Lys Val Ala Val Thr
    130                 135                 140

Gly Gly Lys Val Thr Leu Ser Cys Asn Gln T hr Asn Asn His Asn Asn
145                 150                 155                 160

Met Tyr Trp Tyr Arg Gln Asp Thr Gly His G ly Leu Arg Leu Ile His
                165                 170                 175

Tyr Ser Tyr Gly Ala Gly Ser Thr Glu Lys G ly Asp Ile Pro Asp Gly
            180                 185                 190

Tyr Lys Ala Ser Arg Pro Ser Gln Glu Asn P he Ser Leu Ile Leu Glu
        195                 200                 205

Leu Ala Thr Pro Ser Gln Thr Ser Val Tyr P he Cys Ala Ser Gly Asp
    210                 215                 220

Ala Ser Gly Ala Glu Thr Leu Tyr Phe Gly S er Gly Thr Arg Leu Thr
225                 230                 235                 240

Val Leu Val Thr His His His His His
            245                 250

(2) INFORMATION FOR SEQ ID NO: 7:

(i) SEQUENCE CHARACTERISTICS:
        (A) LENGTH:       747 base pairs
        (B) TYPE:         nucleic acid
        (C) STRANDEDNESS: sin gle
        (D) TOPOLOGY:     linear (xi) SEQUENCE DESCRIPTION: SEQ ID NO : 7:

GACTCAGTGA CTCAGACGGA AGGTCAAGTG GCCCTCTCAG AAGAGGACTT T CTTACGATA      60

CACTGCAACT ACTCAGCCTC AGGGTACCCA GCTCTGTTCT GGTATGTGCA G TATCCCGGA    120

GAAGGGCCAC AGTTCCTCTT TAGAGCCTCA AGGGACAAAG AGAAAGGAAG C AGCAGAGGG    180

TTTGAAGCCA CATACAATAA AGAAGCCACC TCCTTCCACT TGCAGAAAGC C TCAGTGCAA    240

GAGTCAGACT CGGCTGTGTA CTACTGCGCT CTGAGTGAAA ACTATGGAAA T GAGAAAATA    300

ACTTTTGGGG CTGGAACCAA ACTCACCATT AAACCGGGTG GAGGCGGTTC A GGCGGAGGT    360

GGATCCGGCG GTGGCGGATC GGAGGCTGCA GTCACCCAAA GCCCAAGAAA C AAGGTGGCA    420

GTAACAGGAG GAAAGGTGAC ATTGAGCTGT AATCAGACTA ATAACCACAA C AACATGTAC    480

TGGTATCGGC AGGACACGGG GCATGGGCTG AGGCTGATCC ATTATTCATA T GGTGCTGGC    540

AGCACTGAGA AAGGAGATAT CCCTGATGGA TACAAGGCCT CCAGACCAAG C CAAGAGAAC    600

TTCTCCCTCA TTCTGGAGTT GGCTACCCCC TCTCAGACAT CAGTGTACTT C TGTGCCAGC    660

GGTGATGCGT CGGGAGCAGA AACGCTGTAT TTTGGCTCAG AACCAGACTG G ACTGTTCTG    720

GTCACCCATC ACCATCACCA TCACTAA                                        747
```

(2) INFORMATION FOR SEQ ID NO: 8:

(i) SEQUENCE CHARACTERISTICS:
    (A) LENGTH:       248 amino acid residues
    (B) TYPE:         amino acid
    (C) STRANDEDNESS: sin gle
    (D) TOPOLOGY:     linear (xi) SEQUENCE DESCRIPTION: SEQ ID NO : 8:

```
Asp Ser Val Thr Gln Thr Glu Gly Gln Val A la Leu Ser Glu Glu Asp
 1               5                  10                  15

Phe Leu Thr Ile His Cys Asn Tyr Ser Ala S er Gly Tyr Pro Ala Leu
                20                  25                  30

Phe Trp Tyr Val Gln Tyr Pro Gly Glu Gly P ro Gln Phe Leu Phe Arg
            35                  40                  45

Ala Ser Arg Asp Lys Glu Lys Gly Ser Ser A rg Gly Phe Glu Ala Thr
        50                  55                  60

Tyr Asn Lys Glu Ala Thr Ser Phe His Leu G ly Lys Ala Ser Val Gly
 65                 70                  75                  80

Glu Ser Asp Ser Ala Val Tyr Tyr Lys Ala L eu Ser Glu Asn Tyr Gly
                85                  90                  95

Asn Glu Lys Ile Thr phe Gly Ala Gly Thr L ys Leu Thr Ile Lys Pro
               100                 105                 110

Gly Gly Gly Gly Ser Gly Gly Gly Ser G ly Gly Gly Gly Ser Glu
           115                 120                 125

Ala Ala Val Thr Gly Ser Pro Arg Asn Lys V al Ala Val Thr Gly Gly
       130                 135                 140

Lys Val Thr Leu Ser Lys Asn Gly Thr Asn A sn His Asn Asn Met Tyr
145                 150                 155                 160

Trp Tyr Arg Gly Asp Thr Gly His Gly Leu A rg Leu Ile His Tyr Ser
               165                 170                 175

Tyr Gly Ala Gly Ser Thr Glu Lys Gly Asp I le Pro Asp Gly Tyr Lys
               180                 185                 190

Ala Ser Arg Pro Ser Gly Glu Asn Phe Ser L eu Ile Leu Glu Leu Ala
           195                 200                 205

Thr Pro Ser Gly Thr Ser Val Tyr Phe Lys A la Ser Gly Asp Ala Ser
       210                 215                 220

Gly Ala Glu Thr Leu Tyr Phe Gly Ser Gly T hr Arg Leu Thr Val Leu
225                 230                 235                 240

Val Thr His His His His His
                245
```

SECRETION OF T CELL RECEPTOR FRAGMENTS FROM RECOMBINANT *ESCHERICHIA COLI* CELLS

This application is a continuation-in-part of application Ser. No. 07/873,930, filed Apr. 24, 1992, now abandoned, which is is a continuation-in-part of U.S. patent application Ser. No. 07/832,302, filed Jan. 17, 1992, now abandoned.

The United States Government has certain rights in the invention pursuant to the terms of grant no. AI31592 awarded by the National Institutes of Health.

BACKGROUND OF THE INVENTION

1. Field of the Invention

The invention relates to cloning vectors useful for the expression of T-cell variable domains, to bacterial cells transformed by the vectors and to methods of producing T-cell variable domains in a prokaryotic host cell, either as single domains or as single chain heterodimers.

2. Description of Related Art

The production of single or heterodimeric T-cell receptor variable domains is of interest for purposes of studying T-cell receptor interaction with antigens and possibly developing approaches to therapies for autoimmune diseases and cancer. An important goal of molecular biology is a detailed understanding at the molecular level of the binding of T-cell receptors to cognate peptide-major histocompatibility complexes. This will be a step in the development, for example, of immunotherapy for T-cell mediated autoimmune disease. Despite this interest and the potential applications arising from the study of T-cell receptor domains, no methods are available for the production of only single T-cell receptor domains, nor has expression and secretion in prokaryotic hosts been successful.

The majority of T cells recognize antigenic peptides bound to class I or II proteins of the major histocompatibility complex (MHC) and are thus "MHC restricted". The recognition of peptide-MHC complexes is mediated by surface-bound T-cell receptors (TCRs). These receptors are comprised of various heterodimeric polypeptides, the majority of which are $\alpha$ and $\beta$ polypeptides. A minor population (1–10%) of mature T-cells bear T-cell receptors (TCRs) comprising $\delta\gamma$ heterodimers (Borst et al., 1987; Brenner et al., 1986).

Several composite dimeric species incorporating the $\alpha$ and $\beta$ polypeptides have been produced in various systems. TCR $\alpha\beta$ heterodimers have been expressed as phosphatidyl-inositol linked polypeptides (Lin et al., 1990) or TCR-immunoglobulin chimeras (Gregoire et al., 1991) in mammalian transfectomas. The production of $V_\alpha C\kappa$ homodimers (Mariuzza & Winter, 1989) and $V_\beta$-$C\beta$ monomers (Gascoigne, 1990) in mammalian cells has also been described. The expression and secretion of immunoglobulin VH domains (Ward et al., 1989), Fv fragments (Skerra and Pluckthum, 1988; Ward et al., 1989) and Fab fragments (Better et al., 1988) has been reported. Molecular modeling analyses indicate that there are structural similarities between immunoglobulin $F_{ab}$ fragments and the extracellular domains of TCRs (Novotny et al., 1986; Chothia et al., 1988). Several expression systems for the production of recombinant TCRs in mammalian cell transfectomas have been documented but successful expression and secretion of these proteins in a prokaryotic host has not been reported.

Despite apparent expression of a single chain anti-fluorescein TCR in *E. coli* (Novotny et al., 1991), the product could not be isolated from the periplasm even though the leader sequence had been cleaved from the N-terminus of the recombinant protein. The single chain TCR was relatively insoluble, requiring the use of genetic manipulation to replace five of the "exposed" hydrophobic residues with relatively hydrophilic residues.

No methods are presently available for the production of single or heterodimeric T-cell receptor variable domains as secreted proteins. If available, such species would have potential use in the induction of antibodies as protective vaccines, for the therapy of autoimmune disease, and antibodies for targeting idiotypes (T-cell) or T-cell leukemias. Additionally, secretion of T-cell receptor domains from bacterial cell hosts should provide a convenient, economically attractive and rapid route for production of recombinant T-cell receptors.

Advantages of the production of the TCR variable domains in *E. coli* compared with expression of phosphatidyl-inositol linked heterodimers and TCR-immunoglobulin chimeras in mammalian cells are the following: (1) *E. coli* (and other prokaryotic hosts) grow much faster; thus, results of genetic manipulation of the fragments can be analyzed more quickly, (2) use of *E. coli* is much cheaper than mammalian hosts, (3) production of only the TCR variable domains in mammalian hosts has not been reported. For raising anti-idiotypic antibodies (which recognize variable domains only), this is particularly significant.

TCR fragments have been produced in mammalian cells but they are relatively large. Smaller size TCR segments may allow more rapid structural resolution using such techniques as NMR and X-ray crystallography. Since the variable domains are the regions which interact with peptide-MHC complexes, these regions of TCRs are of considerable interest. Additionally, the use of variable domains alone in immunization should result in the production of anti-variable domain antibodies. Such antibodies are expected to be particularly desirable for use in therapy and diagnosis since they block the interaction of the TCR with antigen and, due to the variable nature of the $V_\alpha/V_\beta$ domains or other domains such as $V_\gamma$ and $V_\delta$, are specific for subsets of T-cells. Large TCR fragments, such as those that can be expressed from mammalian cells, result in production of antibodies not only against the variable domains, but also against the TCR constant domains, (if present in the construct) and/or the immunoglobulin domains (if present in the construct). There would therefore be distinct advantages in having smaller variable domain TCR fragments available, particularly for immunization since any immune response generated is likely to be directed to particular regions of interest, i.e., the V domains.

SUMMARY OF THE INVENTION

The present invention seeks to address one or more of the foregoing problems associated with expression and secretion of T-cell receptor variable domains in a prokaryotic host cell. Recombinant $V_\alpha$, $V_\beta$ and single chain $V_\alpha V_\beta$ heterodimers have been produced in gram-negative hosts transformed with vectors containing DNA encoding one or more T-cell receptor variable domains. The T-cell receptor domains are efficiently secreted in *E. coli* or *S. marcescens*. Only the TCR proteins expressed in *E. coli* have been characterized by CD. These products contain a high proportion of β-sheet structure indicative of a native structure. Murine T-cell $V_\alpha$ and $V_\beta$ domains have been expressed and isolated in yields up to milligram quantities per liter of bacterial culture. Single T-cell variable domains ($V_\alpha$ and $V_\beta$)

and single chain (sc) $V_\alpha V_\beta$ heterodimers have been produced employing the disclosed vectors.

The recombinant plasmids or expression vectors of the invention are particularly adapted for expression of T-cell receptor domains in transformed prokaryotic host cells. The recombinant plasmids comprise a DNA segment coding for one or more T-cell receptor variable domains. Any of a number of variable domains may be included but preferred domains are the $V_\alpha$ and $V_\beta$. Murine T-cell receptor domain $V_\alpha V_\beta$ heterodimer, derived from the 1934.4 hybridoma (Wraith et al., 1989) is particularly preferred. Segments of the $V_\alpha$ or $V_\beta$ domains as well as other variable domains such as $V_\gamma V_\delta$, constant domains, $C_\alpha$, $C_{\beta 1}$, $C_{\beta 2}$, $C_\delta$, $C_\gamma$ or immunoglobulin CH1, CH2 and CH3 domains, etc. may also be employed. It is also contemplated that variations of T-cell receptor variable domains also fall within the scope of the invention. Such variations may arise from mutations such as point mutations and other alterations affecting one or more amino acids or the addition of amino acids at the N or C termini. While the invention has been illustrated with murine T-cell receptors, similar strategies are applicable to the receptor domains from other species, including rat, man and other mammals.

Other DNA segments may also be included linked to the variable domains described, for example, one or more recombinant T-cell receptor variable domains of one or more specificities linked to TCR constant domains, immunoglobulin constant domains, or bacteriophage coat protein genes. Once expressed, any of the products herein could be radiolabelled or fluorescently labeled, or attached to solid supports, including sepharose or magnetic beads or synthetic bilayers such as liposomes. The products could also be linked to carrier proteins such as bovine serum albumin. The TCR V domains, or V domains linked to other proteins (such as constant domains), could also be linked synthetically to co-receptors such as the extracellular domains of CD4 or CD8. This could increase the avidity of the interaction of the TCR fragment with cognate peptide MHC complexes.

Cloning vectors are included in one aspect of the present invention. The vectors include a leader sequence, preferably pelB (Better et al., 1988), although other leader sequences may be used, for example, alkaline phosphatase (phoA) or ompA. In a preferred embodiment, the pelB leader segment is modified with a unique restriction site, such as NcoI, allowing insertion of TCR variable domain genes. Introduction of such restriction sites is a convenient means of cloning in a DNA segment in the same reading frame as the leader sequence.

Modification of the leader sequence DNA may be achieved by altering one or more nucleotides employing site-directed mutagenesis. In general, the technique of site specific mutagenesis is well known in the art as exemplified by publications (Carter, et al., 1985). As will be appreciated, the technique typically employs a phage vector which exists in both a single stranded and double stranded form. Typical vectors useful in site directed mutagenesis include vectors such as the M13 phage (Messing, et al., 1981). These phage are readily commercially available and their use is generally well known to those skilled in the art.

Site directed mutagenesis in accordance herewith is performed by first obtaining a single stranded vector which includes within its sequence the DNA sequence encoding a leader sequence, pelB being used herewith. An oligonucleotide primer bearing the desired mutated sequence is prepared, generally synthetically, for example by the method of Cray, et al. (1978). The primer is annealed with the single stranded vector and subjected to DNA polymerizing enzymes such as the *E. coli* polymerase I Klenow fragment. In order to complete the synthesis of the mutation bearing strand, a heteroduplex is formed wherein one strand encodes the original non-mutated sequence and the second strand bears the desired mutation. The heteroduplex may be transformed into a bacterial such as *E. coli*. or *S. marcescens* cells used herein. Clones are screened using colony hybridization and radiolabelled mutagenic oligonucleotide to identify colonies which contain the mutated plasmid DNA (Carter et al., 1985).

Constructs may also include a "tag" useful for isolation and purification of the expressed and secreted polypeptide product. Tags are relatively short DNA segments fused in-frame with a sequence encoding a desired polypeptide, such as the TCR variable domains herein described, which have the function of facilitating detection, isolation and purification. For example, affinity peptides may be encoded by the segments, allowing isolation by selective binding to specific antibodies or affinity resins. Any of a number of tags may be used, including the c-myc tag, $(his)_6$ tag, decapeptide tag (Huse et al., 1989), Flag™ (Immunex) tags and so forth. A number of the tags are also useful for the detection of expressed protein using Western blotting (Ward et al., 1989; Towbin et al., 1978).

$(His)_6$ tags, for example, are preferable for purifying secreted polypeptide products on affinity metal chromatography columns based on metals such as $Ni^{2+}$. The $(his)_6$ peptide chelates $Ni^{2+}$ ions with high affinity. Polypeptide products containing these residues at the N or C termini bind to the affinity columns, allowing polypeptide impurities and other contaminants to be washed away as part of the purification process. Polypeptide products can then be eluted from the column with high efficiency using, for example, 250 mM imidazole.

Peptide tags, or linkers, may also be incorporated into the TCR product. For single chain TCR fragments, preferred linker peptides include a 15-mer, for example, $(gly_4 ser)_3$, or other linkers, such as those described in Filpula and Whitlow (1991).

The invention has been illustrated with prokaryotic host cells, but this is not meant to be a limitation. The prokaryotic specific promoter and leader sequences described herein may be easily replaced with eukaryotic counterparts. It is recognized that transformation of host cells with DNA segments encoding any of a number of T-cell variable domains will provide a convenient means of providing fully functional TCR protein. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of TCR proteins, e.g., baculovirus-based, glutamine synthase based or dihydrofolate reductase-based systems could be employed. Plasmid vectors would incorporate an origin of replication and an efficient eukaryotic promoter, as exemplified by the eukaryotic vectors of the pCMV series, such as pCMV5.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As used herein the term "engineered" or "recombinant" cell is intended to refer to a cell into which a recombinant gene, such as a gene encoding a T-cell receptor variable domain, has been introduced. Therefore, engineered cells are distinguishable from naturally occurring cells which do not contain a recombinant gene that is introduced by transfection or transformation techniques. Engineered cells are thus cells having a gene or genes introduced through the hand of man. Recombinantly introduced genes will either be in the form of a cDNA (i.e., they will not contain introns), a copy of a cDNA gene, genomic DNA (with or without introns; for expression in prokaryotic hosts, the DNA should be without introns), or will include DNA sequences positioned adjacent to a promoter not naturally associated with the particular introduced gene.

Generally speaking, it may be more convenient to employ as the recombinant gene a cDNA version of the gene. It is believed that the use of a cDNA gene will provide advantages in that the size of the gene is generally much smaller and more readily employed to transform (or transfect) a targeted cell than a genomic gene, which will typically be up to an order of magnitude larger than the cDNA gene. However, the inventor does not exclude the possibility of employing a genomic version of a particular gene where desired, for expression in mammalian cells. For prokaryotic host cells, constructs without introns will be used, since prokaryotes do not splice introns and exons into functional mRNA.

Suitable host cells useful in the practice of the invention include gram-negative organisms and might include *Serratia marcescens, Salmonella typhimurium* and similar species. A particularly preferred host cell is *E. coli* and the several variants of *E. coli* that are readily available and well known to those of skill in the art.

A particular aspect of the invention is a method for the production of T-cell receptor variable domains. A gram-negative microorganism host cell is transformed with any of the disclosed recombinant vectors cultured in an appropriate bacterial culture medium to produce T-cell receptor variable domains which are subsequently isolated. Culturing typically comprises both a growing and an induction step. Growing is conveniently performed in such media as Luria broth plus 1% glucose, 4×TY (double strength 2×TY) plus 1% glucose, minimal media plus casamino acids and 5% w/v glycerol with temperatures in the range of 20° C. to about 37° C., preferably between 25–30° C. All media contains ampicillin at a concentration of 0.1–1 mg/ml; to select bacterial cells which contain the expression plasmid. Induction of expression is typically performed at a point after growth has been initiated, usually after 12–16 hours at 30° C. This length of growth results in the cells being in the early stationary phase at the induction stage. If the growth media contains glucose, the cells are pelleted and washed prior to addition of inducer (isopropylthiogalactopyranoside (IPTG) at a concentration of 0.1–1 mM) since glucose inhibits induction or expression. Cells may be grown for shorter periods prior to induction, for example for 6–10 hours, or to the mid-exponential stage of growth. Cells are induced for 5–28 hours. 5–6 hours of induction is a preferred induction time if the protein is to be isolated from the periplasm, since longer induction times result in the protein leaking into the culture supernatant. However, it may be desirable to isolate product from the external medium, in which case one would prefer using longer induction times. Temperatures in the range of 20° C. to 37° C. may be used as growth and induction temperatures, with 25° C. being a preferred induction temperature.

Isolating polypeptide products produced by the microbial host cell and located in the periplasmic space typically involves disrupting the microorganism, generally by such means as osmotic shock, sonication or lysis. Once cells are disrupted, cells or cell debris may be conveniently removed by centrifugation or filtration, for example. The proteins may be further purified, for example, by affinity metallic resin chromatography when appropriate peptide tags are attached to the polypeptide products.

Alternatively, if the induction period is longer than 8 hours (at 25° C., for example), so that the protein leaks into the culture supernatant, cells may be removed from the culture by centrifugation and the culture supernatant filtered and concentrated (for example, 10–20 fold). Concentrated supernatant is then dialyzed against phosphate buffered saline and separation achieved by column chromatography, such as affinity or adsorption chromatography. An example is separation through $Ni^{2+}$-NTA-agarose to separate appropriately tagged proteins such as those carrying a $(his)_6$ tag. When these tags are used in the construction of an expression vector, histidine tags are particularly preferred as they facilitate isolation and purification on metallic resins such as $Ni^{+2}$-NTA agarose.

Also contemplated within the scope of the invention are the recombinant T-cell receptor single-chain variable domain products. These include single chain heterodimers comprising the variable domains $V_\alpha$, $V_\beta$, $V_\gamma$ and $V_{67}$. However, it will be appreciated that modification and changes may be made in the composition of these domains, for example by altering the underlying DNA, and still obtain a molecule having like or otherwise desirable characteristics.

In general, certain amino acids may be substituted for other amino acids in a protein structure without appreciable loss of interactive binding capacity with structures such as, for example, antigen-binding regions of antibodies or receptor sites. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventor that various changes may be made in the coding sequence for the T-cell variable domains without appreciable loss of the biological utility or activity of the encoded protein. It may even be possible to change particular T-cell receptor variable domain residues and increase the interactive ability, i.e., binding affinity of the variable domains for cognate peptide MHC complex.

In making such changes, the hydropathic index of amino acids may be considered. The importance of the hydropathic amino acid index in conferring interactive biologic function on a protein is generally understood in the art (Kyte et al., 1982). It is known that certain amino acids may be substituted for other amino acids having a similar hydropathic index or score and still retain a similar biological activity. Each amino acid has been assigned a hydropathic index on the basis of its hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid may play a role in determining the secondary structure of the resultant protein, which in turn defines the interaction of the protein with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred. It is also conceivable that it may be possible to increase the binding affinity of a T-cell receptor variable domain by changing an amino acid to another which is quite different in hydrophobicity. This may not have an adverse effect on the structure of the protein, since the residues which interact with peptide-MHC complexes are believed to be located in the exposed hypervariable loops of the V domains.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); (0±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still, although not always, obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

As illustrated herein, transformed $E.$ $coli$ host cells will provide good yields of T-cell receptor variable domains. The yields of about 1–2 mg/L for $V_\alpha$, 0.1–0.2 mg/L for $V_\beta$ and 0.5–1 mg/L for the single chain $V_\alpha V_\beta$ heterodimer may be readily scaled up to produce relatively large quantities of these TCR domains in a matter of days, employing, for example, a (his)$_6$ tag for affinity purification with the $Ni^{2+}$-NTA-agarose. Thus the expression system will provide a valuable source of soluble TCR protein for use in immunizations for the generation of anti-clonotypic antibodies, useful, for example, in passive immunization for the treatment of disease. As an example, TCRs expressed on the surface of leukemic T-cells could be expressed as soluble domains and used in immunization to generate anti-TCR antibodies. Such antibodies could be used as targeting reagents in the therapy of T-cell leukemias. It is also conceivable that such soluble TCRs (derived from pathogenic T cells) may be used in vaccination to generate a specific anti-TCR response in vivo for the therapy of autoimmune diseases in a similar way to that reported using peptides derived from TCR V-regions (Vandenbark, et al., 1989; Howell, et al., 1989; Offner, et al., 1991). Moreover, recombinant $V_\alpha$, $V_\beta$, $V_{67}$, $V_\gamma$, single chain $V_\alpha V_\beta$ fragments, domains, or even subfragments thereof, are potentially useful for mapping the TCR residues which are functionally important in binding peptide-MHC complexes.

The present invention shows that scTCR (from $V_\alpha$ and $V_\beta$) derived from the 1934.4 T-cell hybridoma (Wraith et al., 1989) is secreted into the periplasm and may be purified in yields of approximately 0.5–1 mg/L culture using $Ni^{2+}$-NTA-agarose. FIG. 2 shows an SDS polyacrylamide gel analysis of the purification of this protein. For the scTCR in particular, lower growth and induction temperatures of 25–30° C. resulted in higher expression yields. Even higher expression may be achieved with modifications to growth medium and temperature, as recognized by those of skill in the art. For example, lower growth and induction temperatures were found to enhance expression of other recombinant proteins in $E.$ $coli$ (Takagi et al., 1988).

Purification of the herein described murine TCR variable domains may be achieved in many ways, including chromatography, density gradient centrifugation and electrophoretic methods. A particular example of scTCR purification employs an affinity column, made by linking the monoclonal antibody KJ16 (specific for murine $V_\beta 8$: Kappler et al., 1988) to sepharose. For the 1934.4 derived scTCR, purification with this affinity column indicated that the epitope recognized by this monoclonal antibody is in the correct conformational state in the recombinant scTCR.

A rapid method for the production of soluble, heterodimeric TCRs, as presented in the present disclosure, may be readily extended to the production of soluble TCRs of different specificities, derived from other species such as man. This opens up new avenues for immunotherapy and diagnosis, particularly in relation to T cell mediated autoimmune diseases and T-cell leukemias. Also contemplated is the use of random in vitro mutagenesis to alter the residues of recombinant TCR fragments, and to express these fragments as either soluble proteins as disclosed herein or on the surface of bacteriophage (McCafferty et al., 1990). Mutants binding with higher affinity to peptide-MHC complexes may be screened for or selected for using solid surfaces coated with antigen presenting cells and cognate peptide. Such higher affinity mutants would have a large number of applications, for example, in therapy of autoimmune disease as blocking reagents. The TCR fragments are produced in sufficient quantities for a wide variety of tests and studies including, for example, high resolution structural analyses with NMR and X-ray diffraction.

BRIEF DESCRIPTION OF THE DRAWINGS

FIG. 9 shows the nucleic acid and derived amino acid sequence of sc$V_\alpha V_\beta$pelBhis ver. 2.

DETAILED DESCRIPTION OF PREFERRED EMBODIMENTS

Figure 1A:
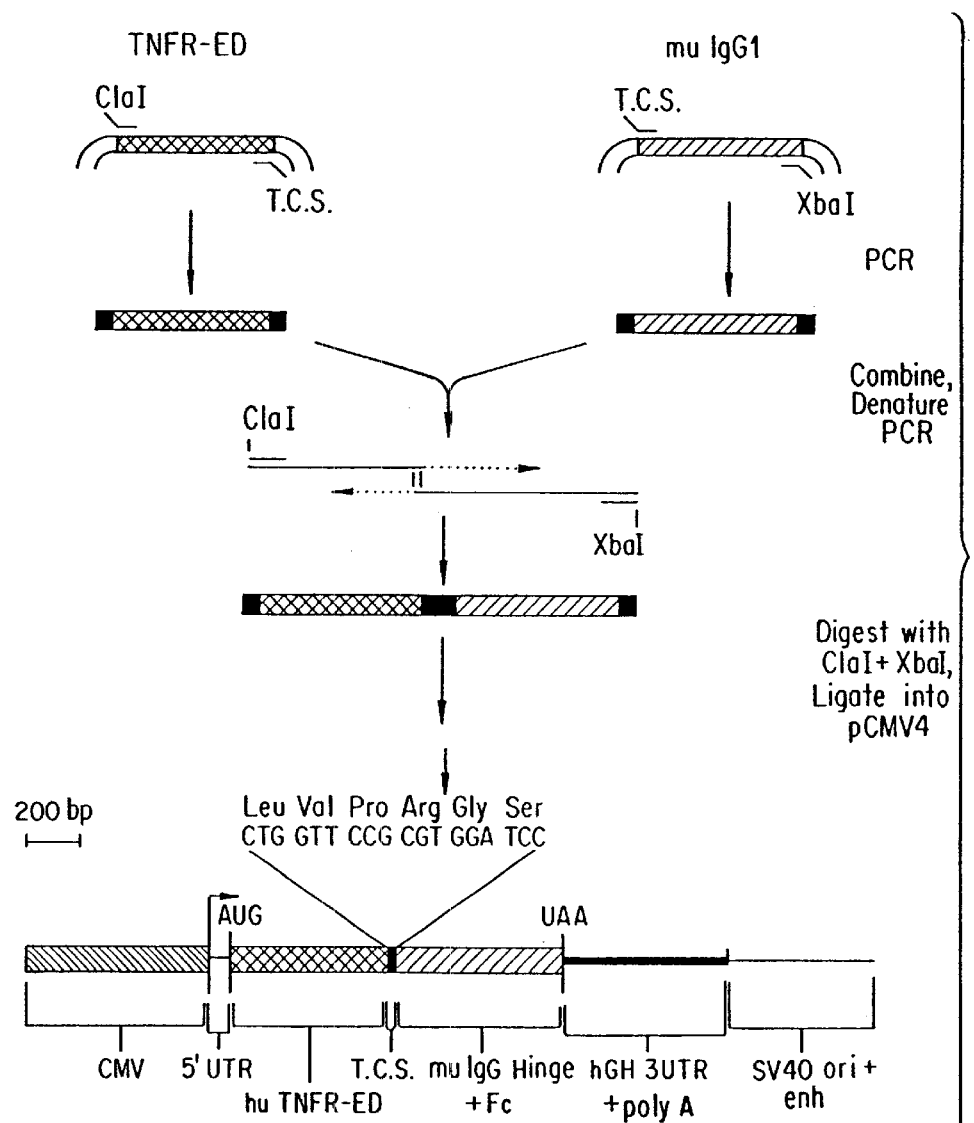
FIG. 1 shows the construction of plasmids for expression of the $V_\alpha$ domain ($V_\alpha$pelBtag1), $V_\beta$ domain ($V_\beta$pelBtag1) and co-expression of the two domains ($V_\alpha V_\beta$pelBtag1). H=HindIII, N=NcoI, B=BstI and E=EcoRI. Filled in box= pelB leader, stippled box=$V_\beta$ gene, striped box=five 3' codons of VH gene in pSWI-VH-poly-tag1 plus tag1 (c-myc) codons, open box=$V_\alpha$ gene and open circle=lacZ promoter.
Figure 1B:
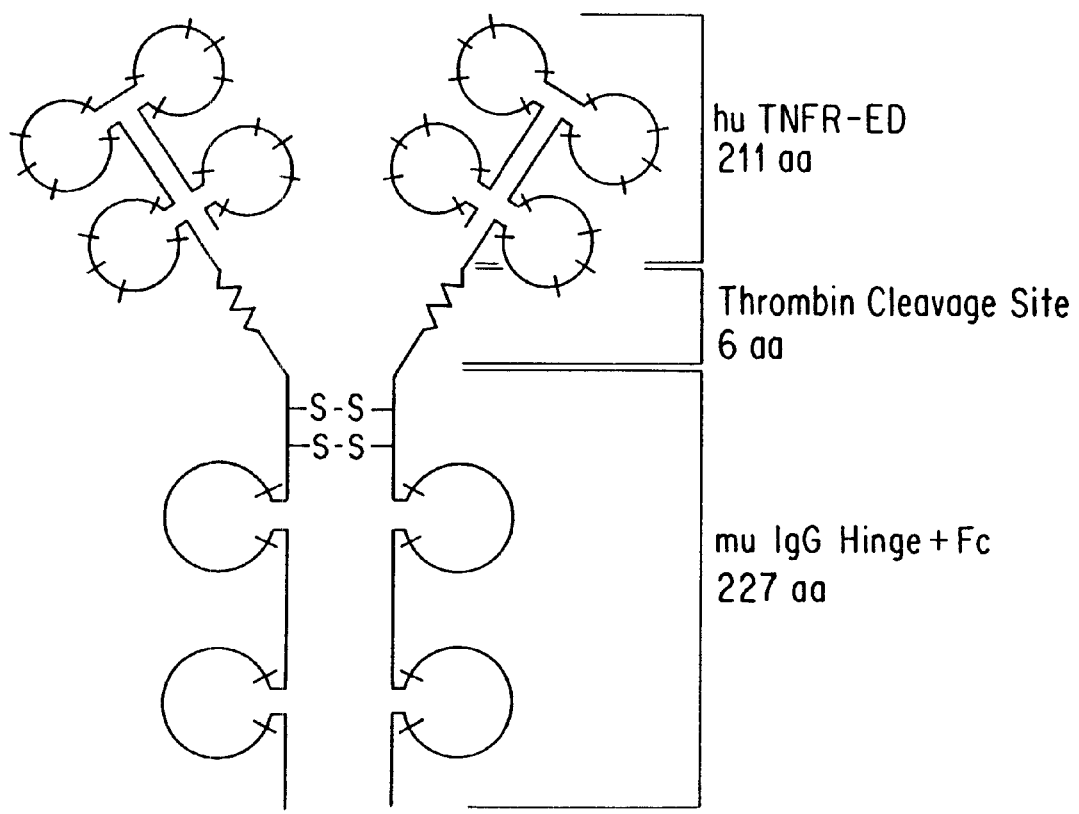
Figures 2A, 2B:
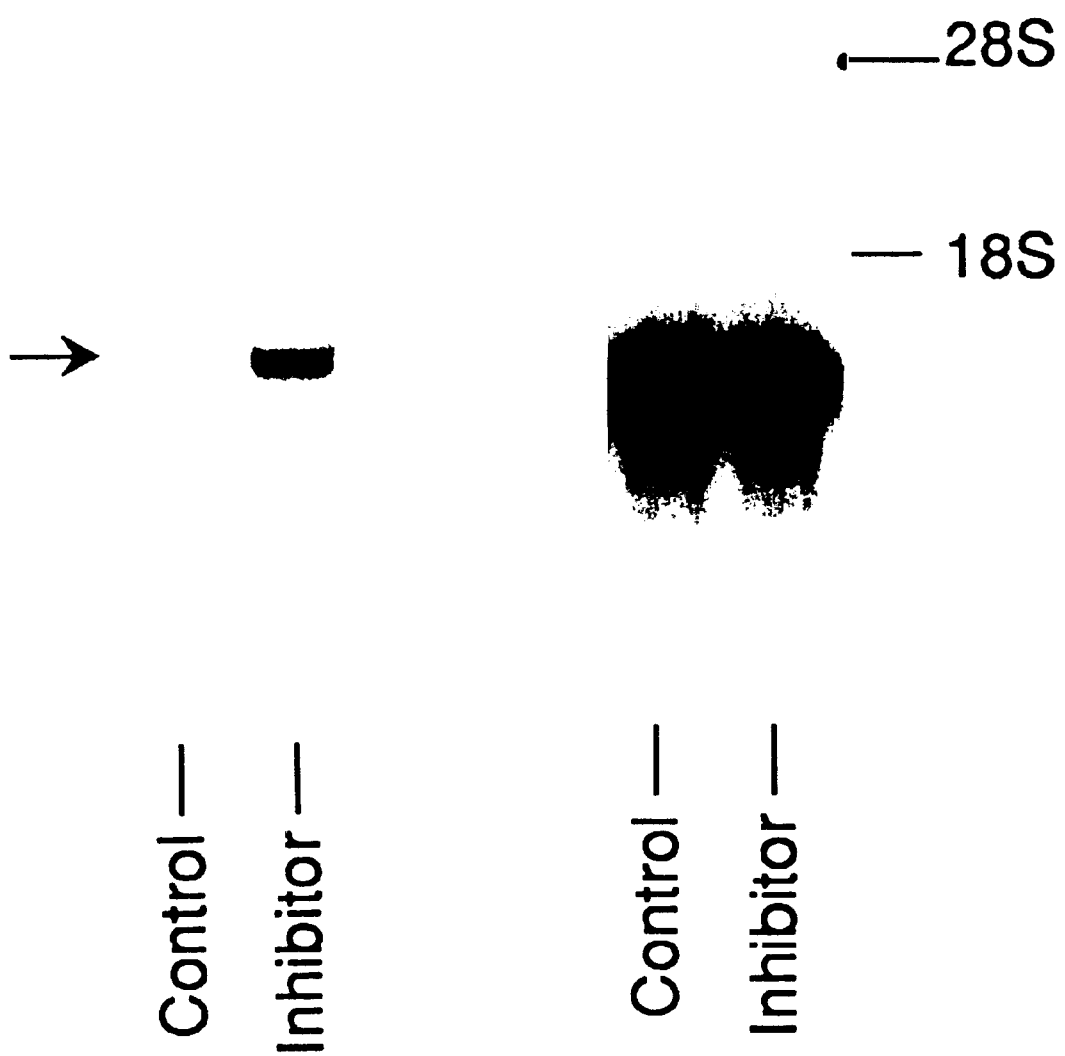
FIG. 2 shows the expression analysis of $V_\alpha$ and $V_\beta$ domains tagged with carboxy terminal c-myc peptides by western blotting (using the 9E10 monoclonal antibody which recognizes the c-myc epitope) of culture supernatants electrophoresed) on a 15% SDS polyacrylamide gel. E. coli recombinants harboring the following plasmids were analyzed: lane 1, $V_\alpha V_\beta$pelBtag1; lane 2, V$\beta$pelBtag1, and lane 3, $V_\alpha$pelBtag1. The mobilities of molecular weight size standards, run on an equivalent gel stained with Coomassie brilliant blue rather than transferred onto nitrocellulose, are indicated in kDa on the right margin.

The present invention concerns the cloning and expression of the variable domains of a murine T-cell receptor (TCR) in a gram-negative bacterial host. The genes encoding the TCR for $V_\alpha$ and $V_\beta$ domains of T-cell hybridoma 1934.4 (Wraith et al., 1989) were isolated using the polymerase chain reaction (Saiki et al., 1988) and ligated into expression vectors constructed from pUC119 (Viera et al., 1987). PUC119 contains a lacZ promoter sequence upstream of the site into which the $V_\alpha$ and $V_\beta$ domain genes were ligated. The new expression vectors included a pelB leader segment in translational frame with the cloned variable domain genes. Modification of these expression vectors, containing $V_\alpha$ and $V_\beta$ single variable domains, was accomplished by cloning a $V_\beta$ encoding segment 3' to a $V_\alpha$ gene segment and incorporating a single chain linker peptide. Bacterial hosts transformed with this construct were capable of expressing single chain heterodimeric TCR $V_\alpha V_\beta$ domains.

The TCR genes employed were derived from a pathogenic CD4$^+$ T-cell clone associated with induction of experimental allergic (autoimmune) encephalomyelitis (EAE) in the H-2$^u$ mouse (Wraith et al., 1989). EAE is a prototypic model of T-cell mediated autoimmune disease and may be a valuable model for multiple sclerosis in humans.

Expression of Single $V_\alpha$ and $V_\beta$ Domains $V_\alpha$ and $V_\beta$ genes derived from 1934.4 cells were cloned into VHNco-poly-tag1 to generate $V_\alpha$pelBtag1 ($V_\alpha$ gene only) and $V_\beta$pelBtag1 ($V_\beta$ gene only) and transformed into E. coli host cells. The nucleotide sequences of the constructions were confirmed by DNA sequencing prior to growing up and inducing E. coli recombinants for expression. Culture supernatants were analyzed by western blotting which clearly showed that the $V_\alpha$ and $V_\beta$ domains were expressed individually and could be secreted into the culture supernatant. The molecular weights, from SDS gel analysis, were estimated as 17 kDa ($V_\alpha$-tag1) and 14.5 kDa ($V_\beta$-tag1). For the $V_\alpha$ domain this is significantly higher than that predicted by amino acid analysis, but is similar to the anomalously low gel mobilities observed for single antibody VH domains. The level of secretion of the $V_\alpha$ domain was particularly high and was similar to, if not greater than, that reported for immunoglobulin FvD1.3 fragment expressed and secreted from E. coli (Ward et al., 1989). The level was estimated at 10 mg per liter of culture, by comparison with culture supernatants of E. coli recombinants harboring pSW1-VHD1.3-VkD1.3-tag1 using western blotting. The relatively high expression level of the $V_\alpha$ domain may reflect a propensity of this domain to form homodimers. Such homodimer formation could mask the hydrophobic residues of the $V_\alpha$ domain which, in a native TCR, interact with analogous $V_\beta$ residues during $V_\alpha$:$V_\beta$ pairing, thus increasing the solubility (and secretion levels) of the homodimer.

In contrast to the $V_\alpha$ domain, the $V_\beta$ domain was secreted into the culture supernatant at levels of about 0.5–1 mg per liter of culture, although the intracellular/periplasmic levels of the $V_\beta$ domain were similar to those of the $V_\alpha$ domain. The $V_\beta$ protein apparently does not fold into a soluble form as readily as the $V_\alpha$ domain. It is expected that the amount of secreted $V_\beta$ will be increased by altering the induction conditions. Alternatively, higher levels of soluble $V_\beta$ domain may be obtained by osmotically shocking the recombinant E. coli cells, followed by denaturation and refolding of the released $V_\beta$ protein.

Co-expression of $V_\alpha$ and $V_\beta$ Domains

As illustrated in Example 2, the $V_\alpha$ and $V_\beta$ domains may be co-expressed and secreted from E. coli recombinants harboring $V_{\alpha V\beta}$pelBtag1. The $V_\alpha$ polypeptide was secreted in excess over the $V_\beta$ domain, indicating that at least some of the recombinant TCR protein is not heterodimeric. However, $V_\alpha$ domain secretion levels were lower when co-expressed with the $V_\beta$ polypeptide than when expressed and secreted as a single domain. This may be due, for example, to limitations on the amount of protein which can be secreted into the *E. coli* periplasm, i.e., $V_\beta$ secretion may compete with $V_\alpha$ secretion. Alternatively, there may be some polarity effects on the expression of the $V_\alpha$ domain, which is 3' to the $V_\beta$ gene in $V_\alpha V\beta$pelBtag1.

The present invention demonstrates that TCR $V_\alpha$ and $V_\beta$ polypeptides can be expressed and secreted from recombinant *E. coli* cells as either individual domains or co-expressed. The secretion system may be employed as a rapid and economically favorable alternative to existing methods for the production of TCRs or TCR-immunoglobulin chimeras in mammalian cell transfectomas.

For purification, the $V_\alpha$ and $V_\beta$ domain s were expressed with carboxy terminal $(his)_6$ tags. As a preferred method of purification, induction conditions were established allowing isolation of the protein from the periplasmic space using osmotic shock. The osmotic shock fractions were dialyzed against phosphate buffered saline overnight at 4° C. with 3 changes, and the dialysate passed through an $Ni^{2+}$-NTA-agarose column. Alternatively, longer induction times were used and the protein purified from the culture supernatant. Concentration of the supernatant was then effected by concentration under high pressure using an Amicon fitration unit followed by overnight dialysis against PBS and passage through a $Ni^{2+}$-NTA-agarose column. Using purification from osmotic shock fractions, yields of 1–2 mg/L $V_\alpha$ domain and 0.1–0.2 mg/L $V_\beta$ were obtained.

The $V_\alpha$ and $V_\beta$ domains do not associate when co-expressed within the same bacterial cell. To drive the association of the two domains, therefore, the $V_\alpha$ domain was linked to the $V_\beta$ domain by a synthetic linker and the two domains expressed as a heterodimeric scTCR fragment. This heterodimer may be expressed with carboxy-terminal $(his)_6$ peptide tags and purified using affinity purification on $Ni^{2+}$-NTA-agarose columns. The purification yields from osmotic shock fractions were 0.5–1 mg/L culture.

To assess the folded state of the recombinant TCR fragments, CD spectral analyses were carried out on the fragments and on the D1.3 single chain Fv fragment. The minima in the curves at 218 nm for these proteins indicate the presence of a high proportion of β-pleated sheet structure (Johnson, 1990). These spectra also indicated a lack of α-helical regions, since α-helical regions result in minima at ~208 nm and 224 nm, and this is consistent with the proposed structural models for TCR extracellular domains (Novotny et al., 1986; Chothia et al., 1988), and the structure of the crystallographically solved D1.3 Fv fragment (Bhat et al., 1990). The maxima at approximately 205 nm in the spectra of the $V_\alpha$ domain and the D1.3 Fv fragment has previously been associated with the presence of an abundance of β-turns.

Overall and in general terms the invention shows that single $V_\alpha$, $V_\beta$ domains and single chain heterodimeric TCRs (scTCRs) derived from an encephalitogenic T cell hybridoma may be expressed and purified in yields ranging from 0.1–2 milligrams per liter of bacterial culture. In addition, structural analysis using CD indicates that the recombinant TCR fragments contain a high proportion of β pleated sheet structures. Although molecular modelling has indicated that the extracellular domains of TCRs may resemble immunoglobulin Fv and Fab fragments in structure (Novotny et al., 1986; Chothia et al., 1988), to date this has not been demonstrated empirically. The ability of the $V_\alpha$, $V_\beta$ domains and heterodimeric scTCR to inhibit the binding of the 1934.4 T cell hybridoma to cognate peptide-MHC complexes (N-terminal residues 1–11 of myelin basic protein associated with the MHC class II protein I-A"; Wraith et al., 1989) is of particular interest because it would demonstrate functional activity of the recombinant proteins. It is conceivable, however, that soluble TCR fragments are ineffective inhibitors of the multivalent, high avidity, interaction (Harding and Unanue, 1990) of T cell borne antigen receptors with peptide-MHC complexes. The tripartite interaction of 'native' TCR on CD4+ T cells with peptide-MHC complexes may be stabilized by contacts between CD4 residues and the MHC class II molecule (Sleckman et al., 1987: Fleury et al., 1991). The absence of this 'co-receptor' in the recombinant TCRs may therefore decrease the avidity of the interaction further.

Materials and Methods

Bacterial Strains and Plasmids. *E. coli* BMH71-18 was used as host for the cloning and expression of TCR domains (Rüther et al., 1981). Plasmid pSWI-VH-poly-tag1 (Ward et al., 1989) was modified by replacing pUC19 with pUC119 (Viera et al., 1987) as the backbone vector. In addition , an NcoI restriction site was inserted into the pelB leader sequence using site directed mutagenesis to generate $V_H$Nco-poly-tag1.

Isolation of $V_\alpha$ and $V_\beta$ Genes. The $V_\alpha$ and $V_\beta$ genes were isolated from 1934.4 hybridoma cells (Dr. D. Wraith, Cambridge University, Department of Pathology, Immunology Division, Level 3 Laboratories Block, Addenbrookes's Hospital, Hills Road, Cambridge CB2 2QQ, UK) using a PCR amplification method. $10^6$ cells were washed once in sterile PBS, then resuspended in 1 ml sterile deionized water and heated at 100° C. for 5 mins. This results in isolation of genomic DNA. Debris was pelleted by centrifugation for 3 minutes at room temperature at 11,000 rpm and 2–10 µl of supernatant used in a PCR reaction with the following $V_\alpha$ or $V_\beta$ specific primers:

$V_\alpha$: I: 5'-ATC CTT CCA TGG CCG ACT CAG TGA CTC AGA CGG AAG GT-3'

II: 5'-AAG GAT <u>GGT GAC</u> CGG TTT ATT GGT GAG TTT GGT TCC-3'

$V_\beta$: III: 5'-ATC CTT <u>CCA TGG</u> CCG AGG CTG CAG TCA CCC AAA GTC CA-3'

IV: 5'-AAG GAT <u>GGT GAC</u> CAG AAC AGT CAG TCT GGT TCC TGA-3'

For each domain, the oligonucleotides encode either an NcoI or BstEII fragment (underlined) to allow restriction enzyme digestion of the PCR products, followed by gel purification using "Geneclean" (BIO 101, Valley Park, Mo. 63088) and ligation as an NcoI-BstEII fragment into $VH_H$Nco-poly-tag1.

PCR conditions were as follows:

3 units Promega Taq polymerase (Promega, Madison, Wis. 53711-5399)

5 µl 10×Promega reaction buffer 25 pmol of each oligonucleotide primer 0.2 mM dNTPs 2–10 µl 1934.4 hybridoma supernatant (crude genomic DNA preparation)

Water to 5 µl

Cycling conditions were 94° C. for 0.5 min, 55° C. for 0.5 min, 72° C. for 1 min with Taq polymerase added at the end of the first cycle, that is, at 72° C. Thirty cycles of PCR were conducted and an additional 3 units of Taq polymerase added after 15 cycles to minimize occurrence of PCR errors. Alternatively, less error-prone polymerases such as Vent™ polymerase (New England Biolabs, Beverly, Ma. 01915-5599) may be used.

The following examples are intended to illustrate the practice of the present invention and are not intended to be limiting. Although the invention is demonstrated with variable murine T-cell $V_\alpha$ and $V_\beta$ domains, other domains will be adaptable to similar constructs as those described hereinabove. Likewise, a variety of tags, linker sequences and leader sequences may be employed depending on the particular purification or isolation methods desired to obtain the polypeptide products.

EXAMPLE 1

The following example illustrates the construction of plasmids for expression of the T-cell receptor single domains, $V_\alpha$ and $V_\beta$ and the single chain $V_\alpha V_\beta$ construct. Two types of plasmids are illustrated; one with a c-myc tag and the other with a $(his)_6$ tag. Other tags could be used.

$V_\alpha$pelBtag1 Plasmid

Figure 3:
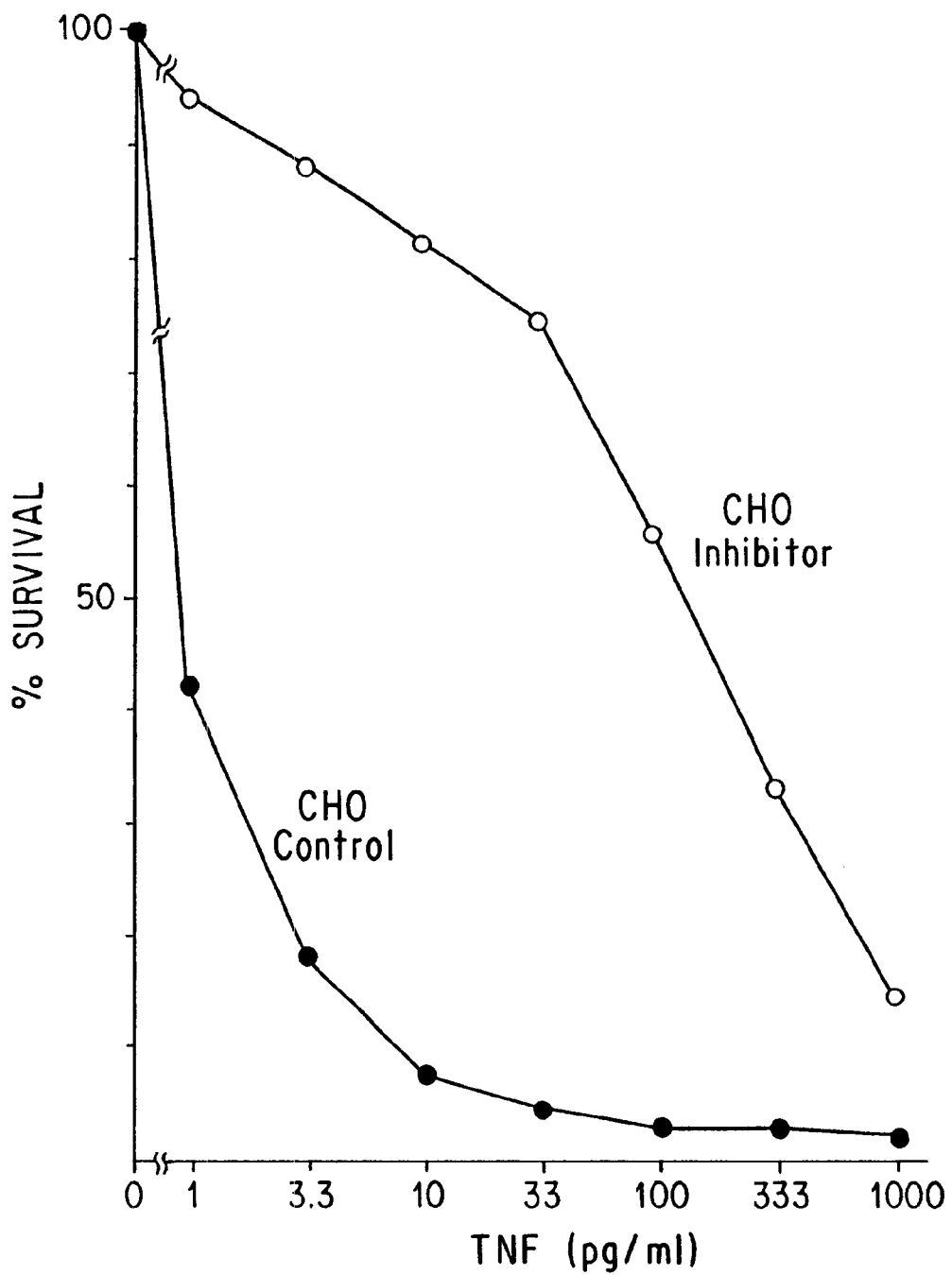
FIG. 3 shows the strategy used for construction of plasmids for expression and purification of single $V_\alpha$ and $V_\beta$ domains and scTCR $V_\alpha V_\beta$ fragments.

The tag portion for the plasmid construct used in this example is c-myc with the following nucleic acid sequence: GAA CAA AAA CTC ATC TCA GA AGA GGA TCT GAAT' encoding the following 11-mer: glu gln lys leu ile ser glu glu asp leu asn. The polylinker sequence is: CTG CAG TCT AGA GTC GAC CTC GAG GGT CACC.

pSWI-VH-poly-tag1 (Ward, et al., 1989) was modified by the insertion of a unique NcoI site into the pelB leader sequence using site-directed dideoxynucleotide mutagenesis (Carter, et al., 1985) and the oligonucleotide 5'-GGC CAT GGC TGG TTG GG-3' to generate VH Nco-poly-tag1. The pelB leader sequence was ATG AAA TAC CTA TTG CCT ACG GCA GCC GCT GGA TTG TTA TTA CTC GCT GCC CAA CCA G<u>CG ATG GC</u>. The underlined portion was converted to CCATGG by mutagenesis. The $V_\alpha$ gene was isolated and tailored by the PCR was then cloned in translational frame as an NcoI-BstEII fragment into VH Nco-poly-tag1 to generate $V_\alpha$pelBtag1 as shown in FIG. 3. Dideoxynucleotide sequencing was carried out to confirm the DNA sequences of the plasmid construction.

$V_\beta$pelBtag1 Plasmid

The $V_\beta$pelBtag1 plasmid was constructed according to the procedure for the $V_\alpha$ plasmid except that the $V_\beta$gene was used in place of $V_\alpha$. The construct is shown in FIG. 3.

$V_\alpha V_\beta$pelBtag1 Plasmid

To construct the $V_\alpha V_\beta$pelBtag1 plasmid, $V_\alpha$pelBtag1 was modified by replacement of the 5' HindIII site of pUC119 (Viera and Messing, 1987) with an EcoRI site by ligation of oligonucleotide V.5'-AGC T<u>GA ATT</u>C 3' as a duplex into HindIII restricted $V_\alpha$pelBtag1 (with the EcoRI site shown underlined). The ligation destroyed the HindIII site. It was then cloned as an EcoRI fragment into EcoRI restricted $V_\alpha$pelBtag1, shown in FIG. 3. Recombinants were analyzed for correct orientation of the $V_\alpha$ gene with respect to the $V_\beta$ gene by restriction enzyme analysis. Dideoxynucleotide sequencing was carried out to confirm the DNA sequences of the plasmid construction.

sc$V_\alpha V_\beta$pelBhis Plasmid

The $V_\alpha$ and $V_\beta$ domains do not associate when they are co-expressed within the same bacterial cell. To drive the association of the two domains, therefore, the $V_\alpha$ domain was linked to the $V_\beta$ domain by a synthetic peptide linker and the two domains expressed as a heterodimeric scTCR fragment. This heterodimer was expressed with carboxy-terminal $(his)_6$ peptide tags and purified as herein described for single chain domains. Purification yields were 0.5–1.0 mg/L culture.

Figure 8:
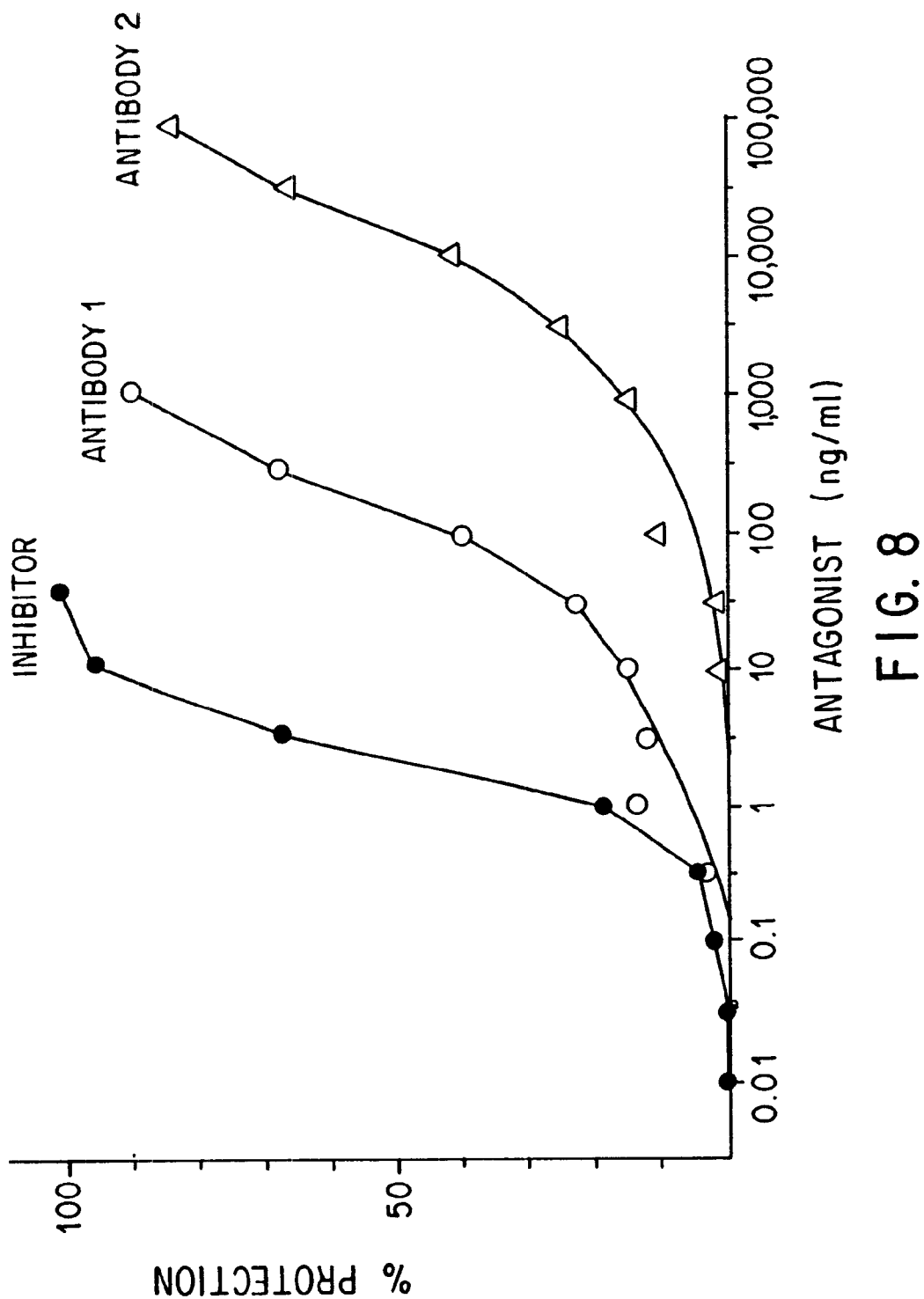
FIG. 8 shows a schematic representation of the plasmid construct for scTCR.
Figure 1:
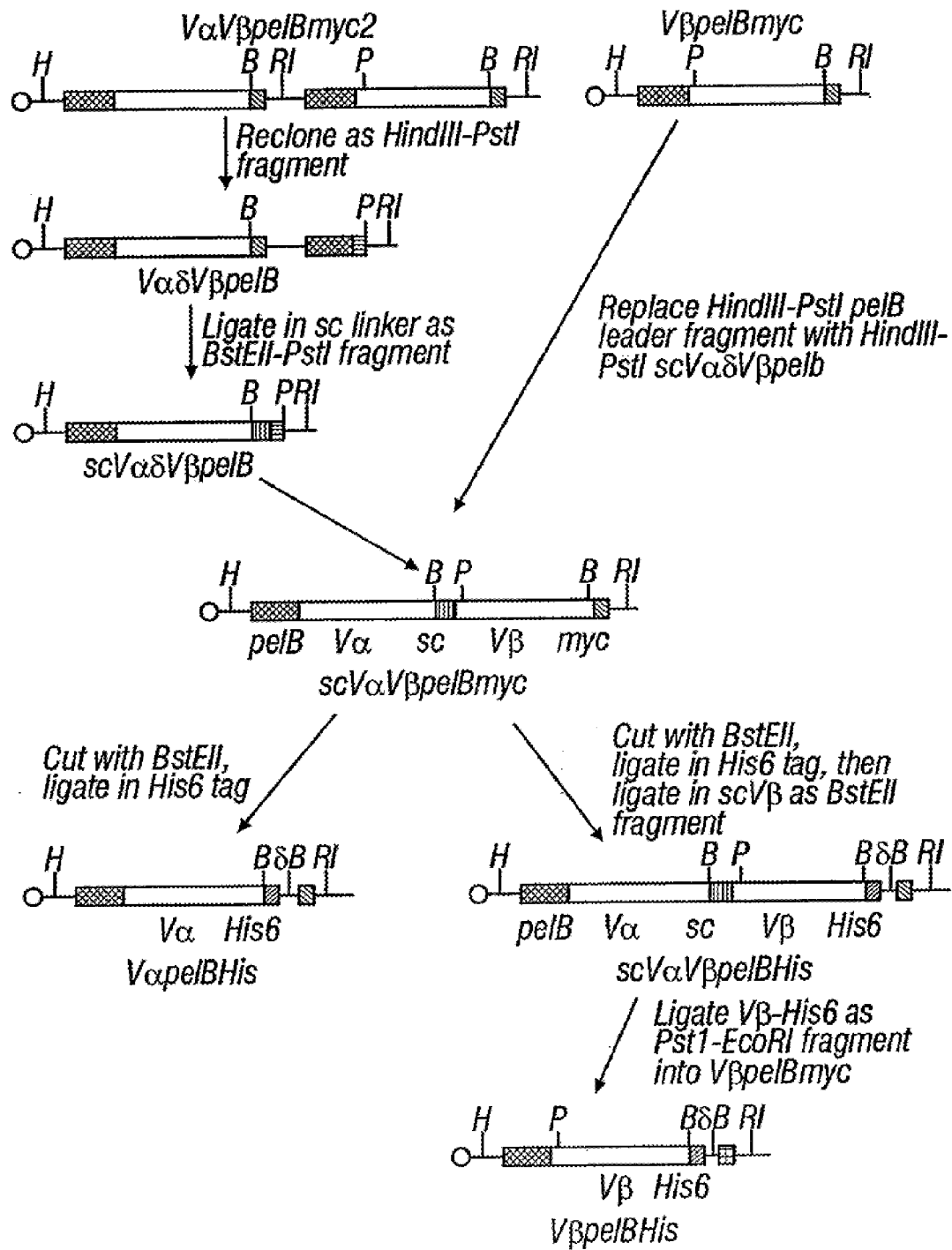

The plasmid $V_\alpha V_\beta$pelBmyc2 (FIG. 1) was constructed in a similar manner to $V_\alpha$pelBmyc or $V_\alpha V_\beta$pelBtag1, except that the $V_\beta$pelBmyc gene was cloned 3' to the $V_\alpha$pelBmyc gene. The plasmid sc$V_\alpha V_\beta$pelBhis, shown schematically in FIG. 8, was constructed as indicated in FIG. 1. The $V_\alpha$ gene was ligated 5' to the $V_\beta$ gene so that in the expressed protein the $V_\alpha$ domain was located at the N-terminus of the $V_\alpha V_\beta$ heterodimer. Since the $V_\alpha$ domain is more soluble than the $V_\beta$ domain and expressed at higher levels, this orientation of the two domains with respect to each other appears to assist in the secretion and folding of the scTCR.

The single chain linker, $(Gly_4Ser)_3$ (Huston et al., 1988) was ligated into BstEIII-PstI restricted $V_\alpha \delta V_\beta$pelB as in the following DNA duplex:

5'-GTC AC<u>C GGT GGA GGC GGT TCA</u>
<u>GGC GGA GGT GGC TCT GGC GGT GGC</u>
3'G CCA CCT CCG CCA AGT CCG CCT CCA CCG
AGA CCG CCA CCG
<u>GGA TCG GAG GCT GCA- 3'</u>
CCT AGC CTC CG-5' where the coding strand is indicated by underlining.

To construct sc $V_\alpha V_\beta$pelBmyc, the resulting HindIII-PstI fragment (sc$V_\alpha \delta V_\beta$pelB) encoding the pelB leader, the $V_\alpha$ gene, the single chain linker and the 5' end of the $V_\beta$ gene was ligated into HindIII-PstI restricted $V_\beta$pelBmyc to replace the pelB leader. To insert the $(his)_6$ peptide tag into sc$V_\alpha V_\beta$pelBmyc, the plasmid was restricted with BstEII and the following duplex ligated into the construct:

5'-GTC <u>ACC CAT CAC CAT CAC CAT CAC TAA</u>
<u>TAA- 3'</u>
3'G GTA GTG GTA GTG GTA GTG ATT ATT CAG
TG-5' with the coding strand indicated by underlining.

Figure 7:
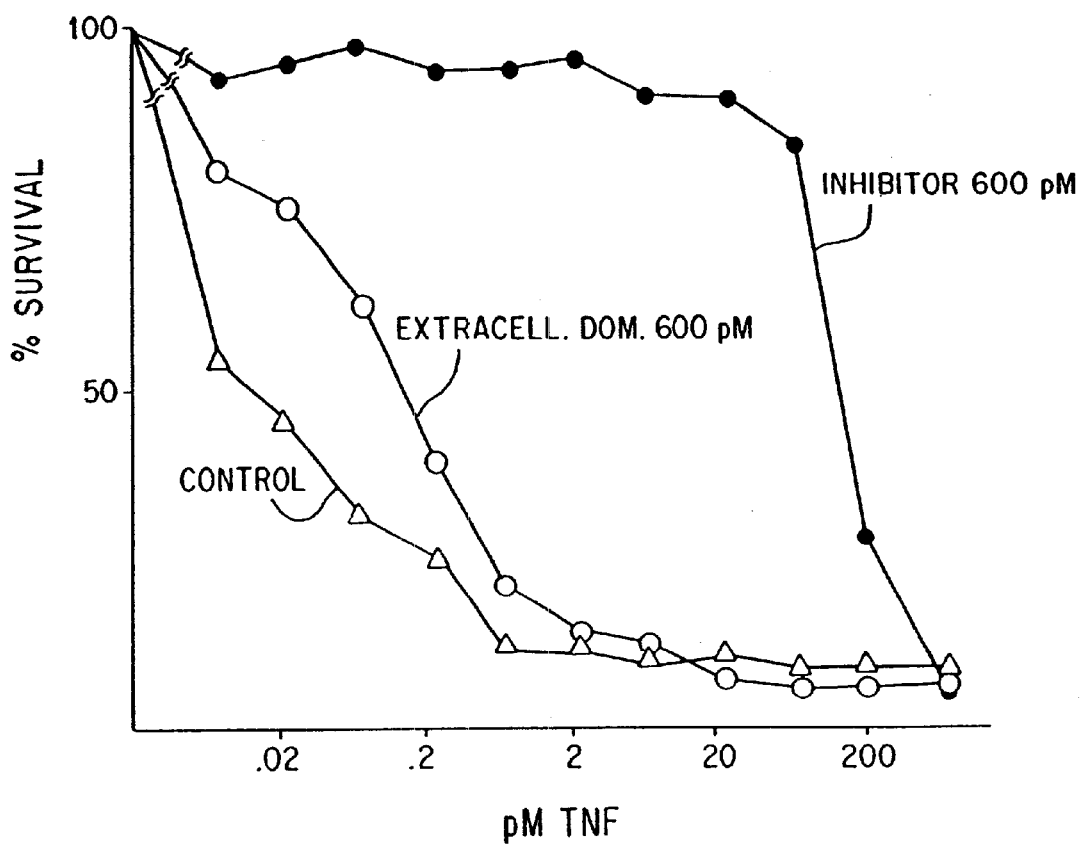
FIG. 7 shows the nucleic acid and derived amino acid sequence of sc$V_\alpha V_\beta$ with the (his)$_6$ tag.

Recombinant clones with the correct orientation of the $(his)_6$ tag were identified by PCR screening. Ligation of the duplex in the correct orientation into BstEII cut sc$V_\alpha V_\beta$pelBmyc removed the 3' BstEII site. In addition, the presence of 2 stop codons at the 3' end of the histidine codons prevented readthrough into the downstream c-myc tag sequences. Nucleic acid and derived amino acid sequences of the single chain TCR with attached $(his)_6$ tag is shown in FIG. 7.

Single stranded DNA was purified from extruded phage using polyethylene glycol precipitation. Sequencing reactions were then carried out using aliquots of the single stranded DNA, appropriate oligonucleotide primers and Sequenase (USB Corp, Cleveland, Ohio 44122) as polymerase. Random low level incorporation of dideoxynucleotides corresponding to each nucleotide position in the gene which was being sequenced occurred by using low levels of chain terminators (dideoxynucleotides) in the reaction mixes. The extended, prematurely terminated single stranded DNA molecules were then analyzed by electrophoresis followed by autoradiography with radiolabeled nucleotides included in the reactions to improve the sensitivity of detection.

Figure 5:
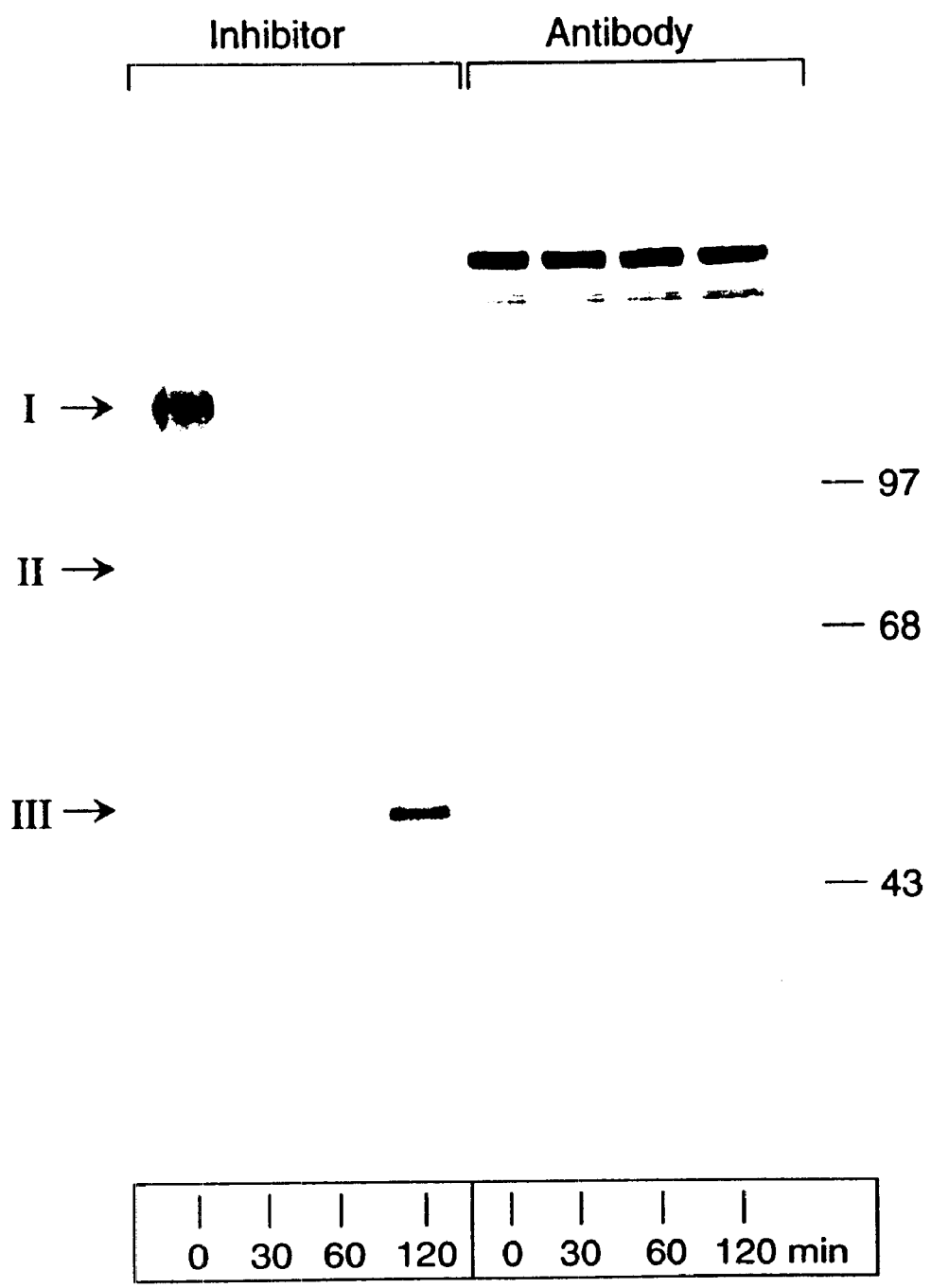
FIG. 5 shows the nucleic acid and derived amino acid sequence of $V_\alpha$ TCR gene with the (his)$_6$ tag.
Figure 6:
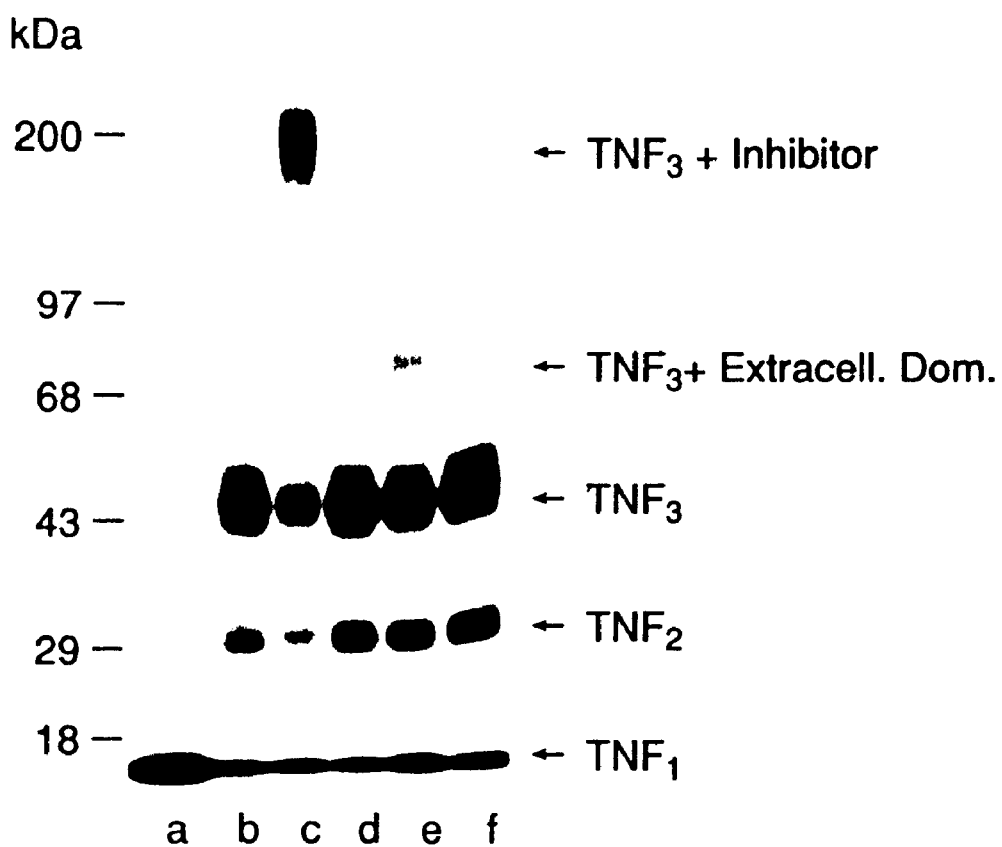
FIG. 6 shows the nucleic acid and derived amino acid sequence of $V_\beta$ TCR gene with the (his)$_6$ tag.

$V_\alpha$pelBhis and $V_\beta$pelBhis were constructed using the strategy shown in FIG. 1. Prior to expression analysis, all DNA constructs were sequenced using the dideoxynucleotide method. Single stranded DNA was isolated from the clones by growth of the recombinant cells in the presence of helper phage, VCSM13 (Stratagene, La Jolla, Calif. 92037). Nucleic acid and derived amino acid sequences for $V_\alpha$pelBhis and $V_\beta$pelBhis are shown in FIGS. 5 and 6 respectively.

$V_\alpha$pelBhis Plasmid $V_\alpha$pelBhis was constructed using the strategy outlined in FIG. 1. This involved restriction by BstEII to remove the single chain linker sequence and the $V_\beta$ domain gene followed by religation.

$V_\beta$pelBhis Plasmid $V_\beta$pelBhis was constructed using the strategy outlined in FIG. 1. A PstI-EcoRI fragment encoding the majority of the $V_\beta$ domain gene and the $(his)_6$ tag was isolated following restriction enzyme digestion. This was then ligated into PstI-EcoRI restricted $V_\beta$pelBmyc to replace the majority of the $V_\beta$ gene and the c-myc tag.

Construction of $scV_\alpha V_\beta$pelBHis ver. 2

Figure 4:
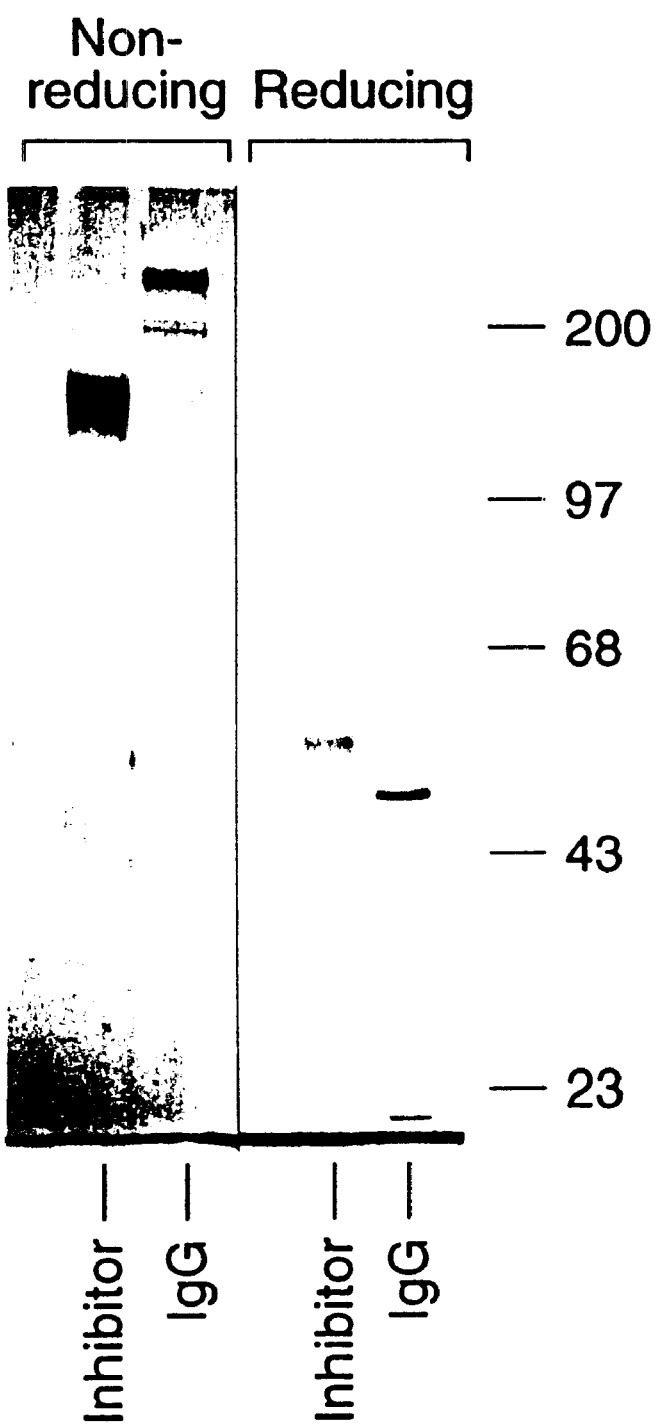
FIG. 4 shows the strategy for the construction of sc$V_\alpha V_\beta$pelBHis ver.2. The pelB leader is represented by a stippled box, the $V_\alpha$ and $V_\beta$ domains by open boxes, the single chain (sc) linker peptide by vertical lines and the (his)$_6$ tag by a hatched box. The lacZ promoter is represented by an open circle. Oligonucleotides A and B are set forth in Example 1. PCR with oligonucleotide B results in the deletion of two codons between the 3' end of $J_\alpha$ and the 5' end of the (gly$_4$ser)$_3$ linker peptide.

A vector $scV_\alpha V_\beta$pelBHis ver. 2 has been constructed in which two codons (val-thr) which are located between the 3' end of the Jα gene and the 5' end of the (gly4ser)$_3$ linker have been removed, FIG. 4. These codons are derived from the 3' end of an immunoglobulin heavy chain variable domain, and may therefore interfere with the scTCR structure in the protein expressed from $V_\alpha V_\beta$pelBHis. The two codons were removed using PCR mutagenesis, as shown in FIG. 4, and the following primers.

Primer A: 5' GTA TCT GCA GCC TCC GAT CCG CCA CCG CCG GAT CCA CCT 3'

Primer B: 5' ATC AGG ATC CAC CTC CGC CTG AAC CGC CTC CAC CCG GTT TAA TGG 3'

The cTCR encoded by $scV_\alpha V_\beta$pelBHis ver. 2 can be secreted and purified in yields of 0.5–1 mg/liter of culture, and CD analysis indicates that the protein is folded into a similar, if not the same, structure as that encoded by sc $V_\alpha V_\beta$pelBHis. Thus, for practical purposes of sc TCR production the two constructs do not appear to differ.

The nucleic acid and derived amino acid sequence of the single chain construct is shown in FIG. 9.

EXAMPLE 2

The following are examples of expression of $V_\alpha$, $V_\beta$ and $V_\alpha V_\beta$ T-cell receptor domains employing *E. coli* hosts transformed with the vectors of Example 1.

Expression of $V_\alpha$, $V_\beta$ and $scV_\beta V_\beta$ Proteins.

Detection of unpurified recombinant protein in culture supernatants or osmotic shock fractions was performed as follows:

*E. coli* recombinants harboring $V_\alpha$pelBmyc, $V_\beta$pelBmyc $V_\alpha V_\beta$pelBmyc, or $scV_\alpha V_\beta$pelBmyc were grown up in 2×TY (or 4×TY) plus 100 μl ampicillin and 1% (wt:vol) glucose to early stationary phase, pelleted by centrifugation, washed once in either 2×TY (or 4×TY) or 50 mM NaCl and then induced by resuspension in 2×TY (or 4×TY) plus 100 μ/ml ampicillin and 1 mM isopropyl-β-D-thiogalactopyranoside (IPTG) for 14–16 hrs. Cultures were grown and induced at 37° C. with shaking at 250 rpm. Culture supernatants were analyzed by western blotting (Towbin et al., 1979; Ward et al., 1985) using monoclonal antibody 9E10 (Evan et al., 1985) followed by anti-mouse $F_c$ conjugated to horseradish peroxidase (ICN Immunobiologicals) for detection. Diamino benzidine (Sigma, St. Louis, Mo.) was used as the horseradish peroxidase substrate. To detect expressed proteins in osmotic shock fractions the following procedure was followed.

Figure 2:
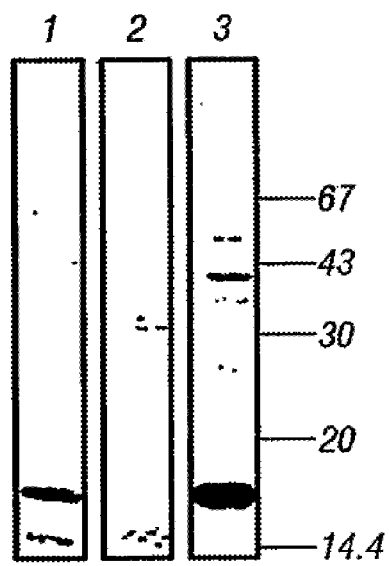
Figure 3:
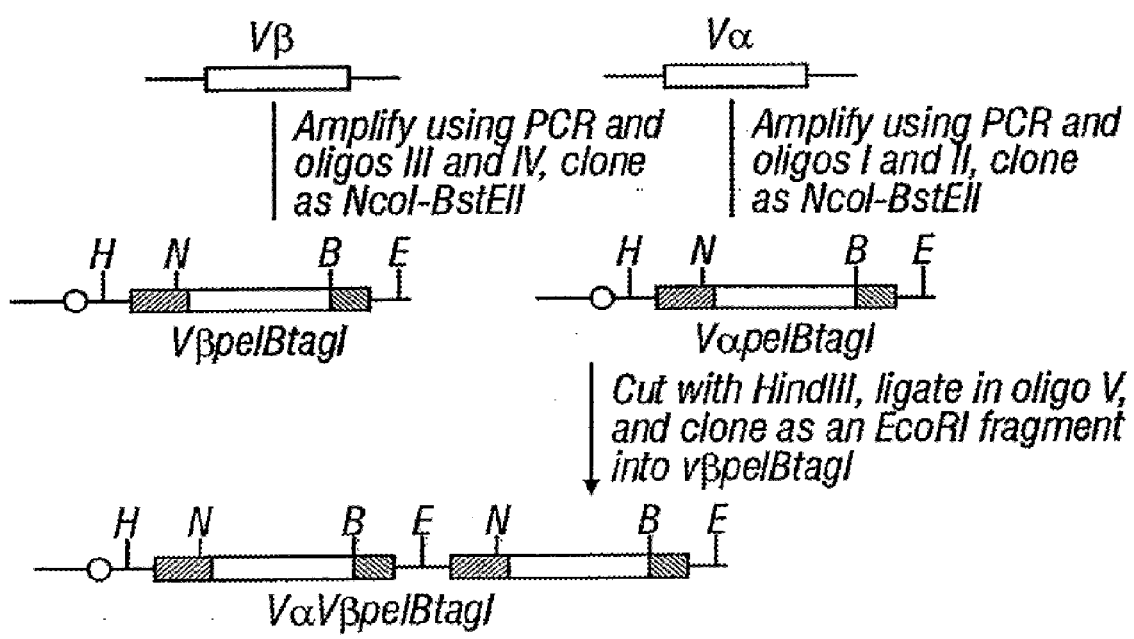
Figure 4:
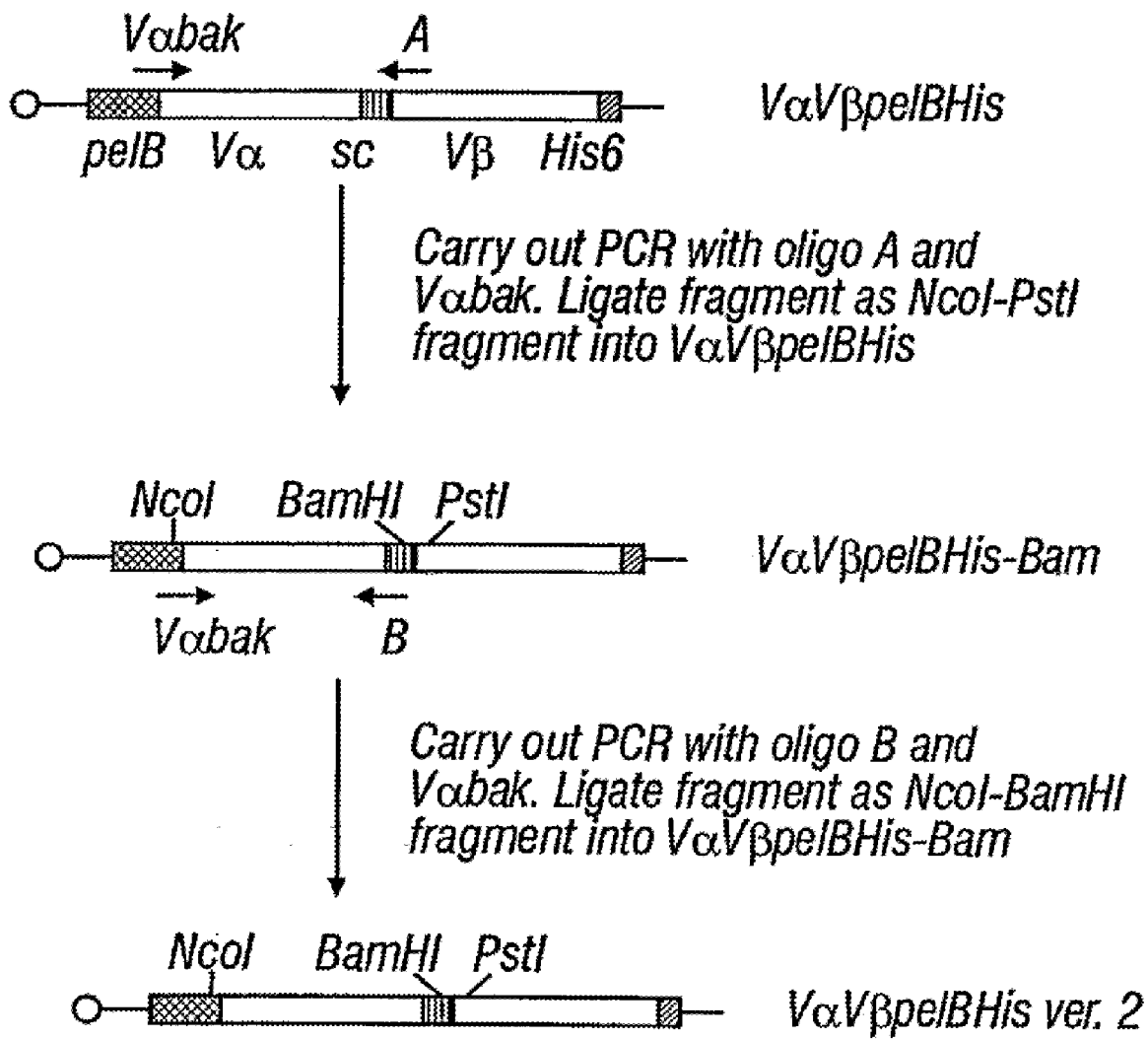
Figure 8:
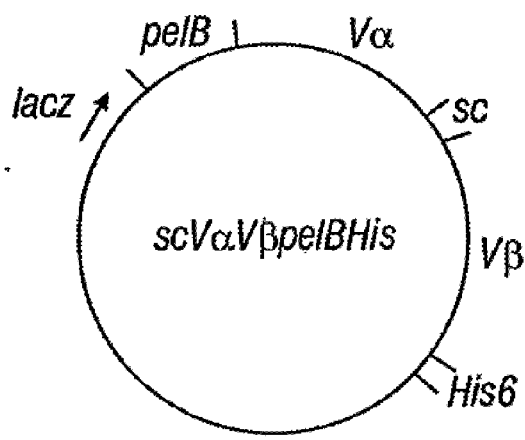
Figure 10:
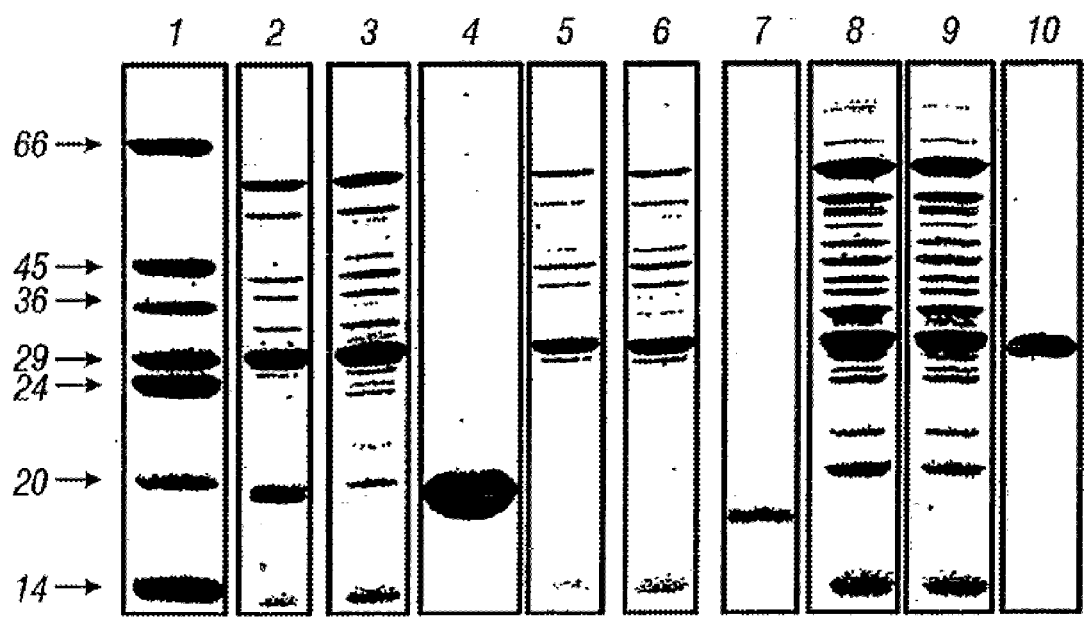
Figure 11A:
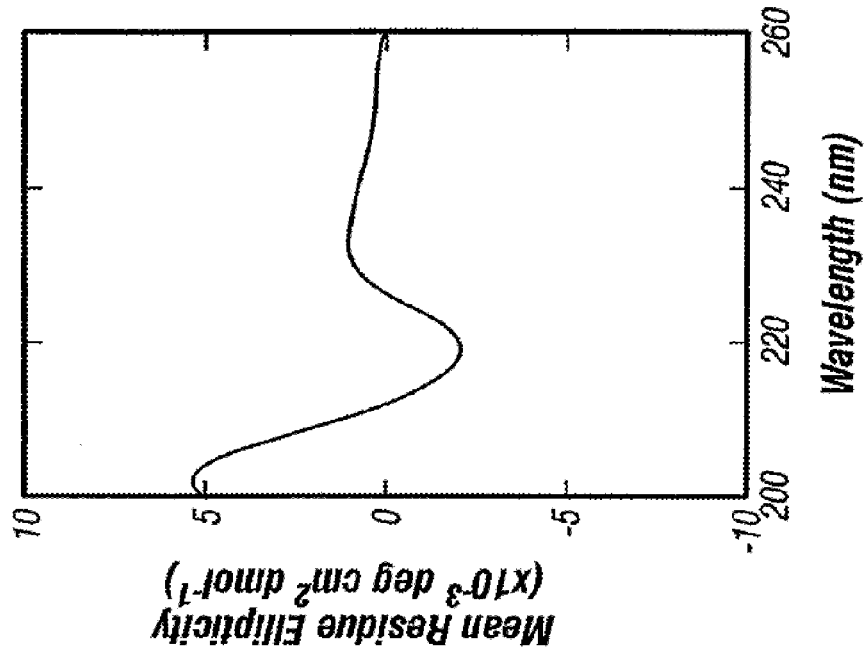
Figure 11B:
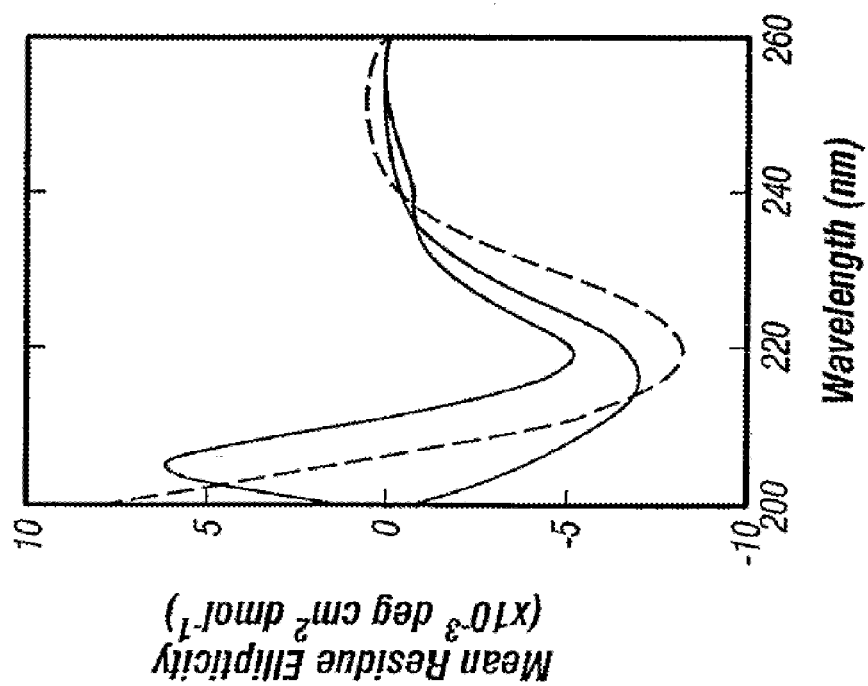

Recombinant cells harboring $V_\alpha$pelBmyc, $V_\beta$pelBmyc, $V_\alpha V_\beta$pelBmyc or $scV_\alpha V_\beta$pelBmyc were grown up at 30° C. for 12–16 hours in the same media as above, pelleted by centrifugation and washed in either 4×TY or 50 mM NaCl, and resuspended in 4×TY plus 100 μg/ml ampicillin plus 0.1 mM IPTG plus 1 mg/ml leupeptin (a protease inhibitor) and 10 μg/ml PMSF for 5–6 hours. Periplasmic fractions were isolated using cold-TES buffer or 20% TES as described below. Osmotic shock fractions (see below) were then analyzed using Western blotting and the 9E10 monoclonal antibody as above. FIG. 2 shows the results of western blotting for $V_\alpha$, $V_\beta$ and $scV_\alpha V_\beta$ domains tagged with carboxy terminal c-myc.

Figure 10:
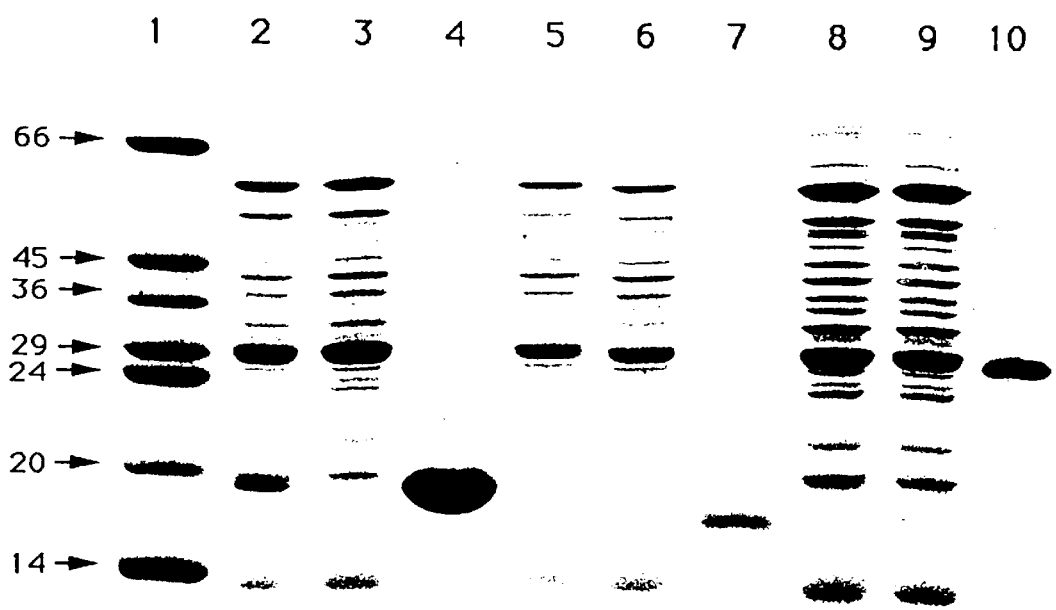
FIG. 10 shows the SDS PAGE analysis of the purified single domains (lanes 2–7) and scTCR (lanes 8–10). Lane 1: molecular weight markers (with sizes shown on the left margin in kDa; lane 2, osmotic shock fraction of E. coli harboring $V_\alpha$pelBhis; lane 3, flowthrough from $V_\alpha$pelBhis osmotic shock fraction after passage through Ni$^{2+}$-NTA agarose column: lane 4, purified $V_\alpha$ domain; lanes 5–7, same as lanes 2–4 respectively, except that E. coli harbors $V_\beta$pelBhis; lanes 8–10, same as lanes 2–4, respectively except that E. coli harbors sc$V_\alpha V_\beta$pelBhis.

For optimal yields of purified T-cell receptor proteins, recombinants harboring $V_\alpha$pelBhis, $V_\beta$pelBhis and $V_\alpha V_\beta$pelBhis were employed. 1–2 liter cultures of recombinants were grown up in 4×TY media (double strength 2×TY) plus 100 μg ampicillin/ml plus 1% (w/v) glucose for 15 hr at 30° C. Cells were pelleted by centrifugation, washed once in 4×TY and resuspended in 1 liter of 4×TY plus 100 μg ampicillin/ml, 0.1 mM-IPTG, 1 μg leupeptin/ml and 10 μg PMSF/ml and grown at 25° C. for 5–5.5 hrs. At this stage the majority of the recombinant protein was located in the periplasm, and was isolated by osmotically shocking the cells as follows:

Cells were cooled by standing on ice for 10 minutes, and then pelleted by centrifugation (6000 rpm, 15 minutes at 4° C.). Cell pellets were resuspended in cold (at 0–4° C.) 200 mM Tris-HCl pH 8.0, 500 mM sucrose and 0.5 mM Na$_2$EDTA (TES, 40 mls used per 1 liter culture). Cells were incubated in TES for 20–40 minutes at 0° C.), and then pelleted by centrifugation (10,000 rpm, 10 minutes at 4° C.). The supernatant was dialyzed against phosphate buffered saline overnight (3 changes at 4° C.). The pellets were resuspended in cold 20% v/v TES and incubated for 20–40 minutes at 0° C. The cells were again pelleted by centrifugation (10,000 rpm, 10 minutes at 4° C.), and the supernatant was dialyzed against phosphate buffered saline overnight (3 changes at 40). Both TES and 20% TES supernatants were then passed through Ni$^{2+}$-NTA-agarose columns. Bound protein was batch eluted in 1–2 ml fractions with 250 mM imidazole, pH 9.2. To reduce non-specific binding of additional proteins, the column was washed with 500 mM NaCl/100 mM Tris HCl, pH 8, and the same at pH 7.4, prior to elution. The purified protein was dialyzed extensively against 10 mM NaH$_2$PO$_4$, pH 7.0, prior to CD analysis. Purity of T-cell receptor fragments was assessed by 15% SDS/polyacrylamide gel electrophoresis followed by staining with Coomassie brilliant blue. The SDS-PAGE stained gel of the purified proteins is shown in FIG. 10.

Yields of the purified $V_\alpha$ and $V_\beta$ domains were approximately 1–2 mg/L culture and 0.2 mg/L culture respectively. Crosslinking experiments with dithiobis (succinimidylpropionate) (DSP) indicated that the $V_\alpha$ domain tended to form homodimers. To analyze the oligomeric state of the $V_\alpha$ domain, the purified protein (at a concentration of approximately 1 mg/ml in PBS) or culture supernatant from induced cultures (see above; 24 hours or more induction) was used. The purified protein was $V_\alpha(his)_6$ (carboxy terminal $(his)_6$ tag) and the culture supernatant contained $V_\alpha myc$ (carboxy terminal c-myc tag). 50 μl of each sample was incubated with 0.1–2 mM of DSP for one hour at room temperature. The crosslinked samples were then analyzed by SDS-PAGE (under non-reducing conditions) followed by either staining with Coomassie brilliant blue (for $V_\alpha(his)_6$) or Western blotting (for $V_\alpha myc$). For the Western blotting, the $V_\alpha$ domain was detected using the 9E10 monoclonal antibody as above. For a significant proportion of $V_\alpha$ domain, the size following incubation with crosslinker was approximately 30 kDa, indicating the formation of homodimers.

As a single chain polypeptide, the 1934.4 hybridoma cell-derived scTCR with a $(his)_6$ peptide tag was secreted into the periplasm and purified using $Ni^{2+}$-NTA-agarose in yields of about 0.5–1.0 mg/l culture. The lower growth and induction temperature and lower IPTG concentration (0.1 mM), about 25° C., was particularly beneficial in inducing higher expression yields for the single chain $V_\alpha V_\beta$ heterodimer.

An alternative purification of the single chain $V_\alpha V_\beta$ domain employed an antibody-linked sepharose column. The purification of the scTCR by affinity chromatography indicated epitopic recognition by the antibody employed, monoclonal antibody KJ16 which is specific for murine $V_{\beta\gamma}$ (Kappler et al., 1988).

EXAMPLE 3

The following example illustrates that the expression vectors of Example 1 are not limited to expression in *E. coli*. Serratia marcescens was employed as host in the following example.

Expression and Secretion of TCR Single Chain TCRs from *S. marcescens*

The plasmid $scV_\alpha V_\beta pelBhis$ was transformed into *S. marcescens* by electroporation and transformants selected on 2×TY agar plates with 1mg/ml ampicillin and 1% w/v glucose, or minimal media (Sambrook et al., 1989) plates plus 1 mg/ml ampicillin plus 1% w/v glucose. Transformants were grown up in minimal media plus 10% w/v casamino acids, 5% w/v glycerol, 0.5 mg/ml ampicillin (MCGA media) at 30° C. for 24 hrs with aeration (250 rpm). 30–50 ml of this culture was used to inoculate 500 ml of the same MCGA media and grown for 12–16 hrs overnight at 30° C. with aeration (250 rpm) and then IPTG added to a final concentration of 0.2–0.5 mM. Cells were induced for 12–24 hrs by growth at 30° C. with aeration (250 rpm). and then stood on ice for 10 min. Cells were pelleted by centrifugation for 30 min, 10,000 rpm, followed by 30 min at 14,000 rpm and the supernatant filtered through a 0.45 μm filter unit (Nalgene). The supernatant was concentrated 10–20 fold in a high pressure concentrator with a YM10 filter and then dialyzed overnight (3 changes) against PBS at 4° C. The dialyzed supernatant was passed through a $Ni^{2+}$-NTA-agarose column using the procedure for isolation from *E. coli* host according to Example 2.

Alternatively, the *S. marcescens* recombinants may be induced for shorter time periods and the protein isolated from the periplasmic space by osmotic shocking. Yields are higher if longer induction periods are employed and the protein isolated from culture supernatant.

EXAMPLE 4

The folded state of the recombinant TCR fragments was assessed by circular dichroism (CD) analysis. Results indicated significant proportion of β-sheet structure, strongly suggesting native folding.

Circular Dichroism Analysis of Expressed TCR Proteins

Figure 11:
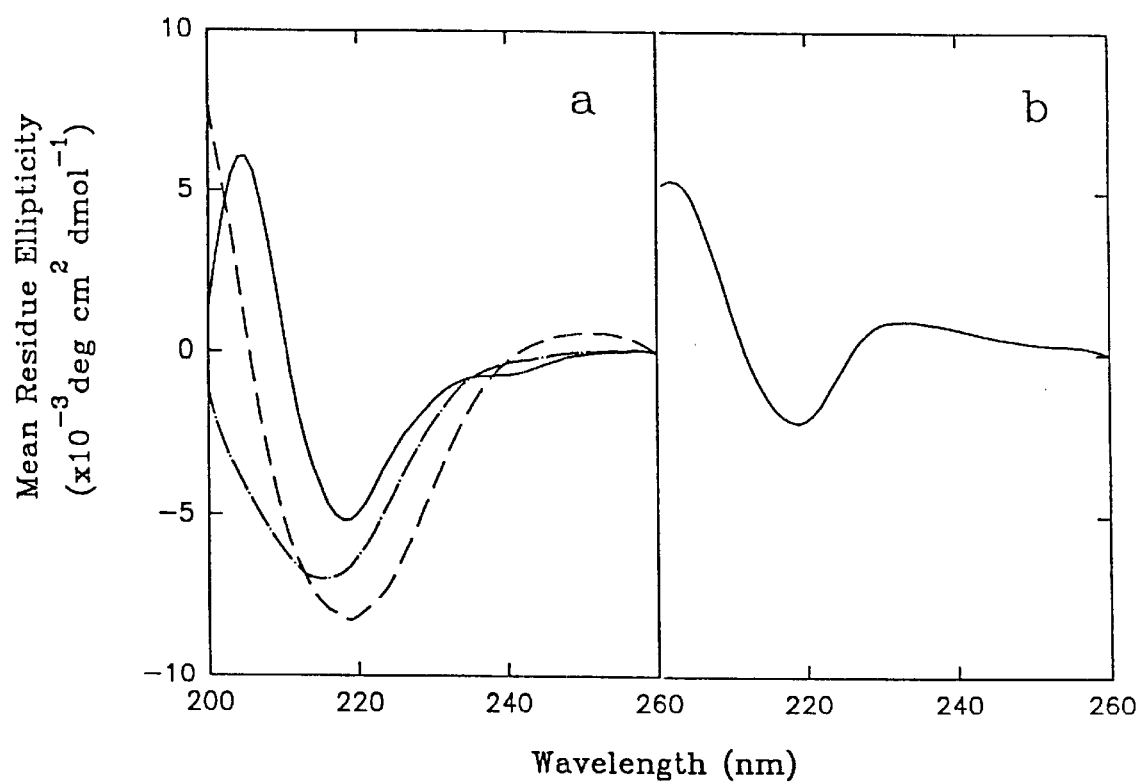
FIG. 11 shows the circular dichroism spectra for the recombinant TCR proteins. Panel A: spectrum for the $V_\alpha$ domain is represented by a solid line; $V_\beta$ by a broken line; and scTCR by a dashed and dotted line. Panel B: spectrum for the D1.3 scFv fragment. All spectra were smoothed and baseline corrected.

FIG. 11 shows the circular dichroism specta of recombinant TCR proteins. The recombinant TCR fragments were purified using the methodology described above, from *E. coli* cells harboring $V_\alpha pelBhis$, $V_\beta pelBhis$ and $scV_\alpha V_\beta pelBhis$ and dialyzed into 10 mM sodium phosphate pH7.0 prior to CD analysis. As a comparison, the immunoglobulin scFv fragment derived from the D1.3 antibody (Ward et al., 1989) was purified and used. This fragment was expressed from a plasmid construction derivative of pSW2 (Ward et al., 1989; McCafferty et al., 1990). The scFv was purified from the culture supernatant of induced cultures using lysozyme sepharose (Ward et al., 1989) and dialyzed against 10 mM sodium phosphate pH 7.0 prior to analysis in CD. The rationale for using this immunoglobulin fragment as a comparison is that molecular modeling indicates that the $V_\alpha$ and $V_\beta$ domains of TCRs resemble immunoglobulin variable domains (Chethi et al., 1988; Novotny et al., 1986). For each recombinant TCR protein, several spectra were generated using different concentrations and/or protein from different purification batches. FIG. 5 shows representative spectra.

CD analyses were carried out using an AVIV model 60DS circular dichroism spectrophotometer at 25° C. and a cell path of 0.2 cm. Concentrations of proteins in 10 mM $NaH_2PO_4$ varied from 1.0 μM to 7.8 μM. Concentration of the purified proteins was determined by quantitative amino acid hydrolysis. Proteins examined were $V_\alpha(his)_6$, $V_\beta(his)_6$, $scTCRV_\alpha V_\beta(his)_6$ and D1.3scFv.

By comparison with both the CD spectrum of the structurally solved D1.3 Fv fragment (Bhat et al., 1990) and that of other proteins known to have a high proportion of β-pleated sheet structure, it was concluded that the CD spectra of the recombinant TCR fragments contained a high proportion of β-pleated sheet structure. This is consistent with the molecular modeling studies which indicate that the TCR domain fold is immunoglobulin-like in character (Chothia et al., 1988; Novotny et al., 1986). The features of the spectra are: i) a minima at 218 nm, indicative of β-pleated sheet structure, ii) no minima at the wavelengths which are characteristic of α helical structure (Johnson, 1990), implying that there is no α helical structure in the TCR domains which is consistent with molecular models, iii) no maxima at the wavelength expected for random coil structure (Johnson, 1990), indicating that at least the majority of the TCR domains are folded into secondary structure and not in denatured (unfolded) state, and iv) for the $V_\alpha$ domain, a maxima at 205 nm indicating the presence of β turns.

REFERENCES

The references listed below are incorporated herein by reference to the extent that they supplement, explain, provide a background for or teach methodology, techniques, and/or compositions employed herein.

Adelman, J. P., Hayflick, J. S., Vasser, M. and Seebury, P. H. *DNA* 2/3, 183–193 (1983).

Better, M., Chang, C. P., Robinson, R. R. and Horwitz, A. H. *Science*, 240, 1041–1043 (1988).

Bhat, T. N., Bentley, G. A., Fischmann, T. O., Boulot, G. and Poljak, R. J. *Nature*, 347, 483–485 (1990).

Borst et al., 1987, *Nature* 325, 683–688.

Brenner et al., 1986, *Nature* 322, 145–149.

Carter, P. J., Bedouelle, H., Winter, G. *Nucleic Acids Res.*, 13, 4431–4443 (1985).

Chothia, C., Boswell, D. R. and Lesk, A. M. *EMBO J.*, 7, 3745–3755 (1986)

Cray, . . . (1978)

Devaux, B., Bjorkman, P. J., Stevenson, C., Greif, W., Elliot, J. F., Sagerström, C., Clayberger, C., Krensky, A. M. and Davis, M. M. *Eur. J. Immunol.*, 21, 2111–2119 (1991).

Evan, G. I., Lewis, G. K., Ramsay, G. and Bishop, J. M. *Mol. Cell. Biol.*, 5, 3610–3616 (1985).

Fleury, S., Lamarre, D., Meloche, S., Ryu, S-E., Cantin, C., Hendrickson, W.A. and Sekaly, R-P. *Cell*, 66, 1037–1049 (1991).

Gascoigne, N. R. J. *J. Biol. Chem.*, 265, 9296–9301 (1990).

Gregoire, C., Rebai, N., Schweisguth, F., Necker, A., Mazza, G., Auphan, N., Millward, A., Schmitt-Verhulst, A-M. and Malissen, B. *Proc. Natl. Acad. Sci. USA*, 88, 8077–8081 (1991).

Harding, C. V. and Unanue, E. R. *Nature*, 346, 574–576 (1990).

Howell, M. D., Winters, S. T., Olee, T., Powell, H. C., Carlo, D. J., Brostoff, S. W. *Science*, 246, 668–670 (1989).

Huston, J. S., Levinson, D., Mudgett-Hunter, M., Tai, M-S, Novotny, J., Margolies, M. N., Ridge, R. J., Bruccoleri, R. E., Haber, E., Crea, R. and Opperman, H. *Proc. Natl. Acad. Sci. USA*, 85, 5879–5883 (1988).

Johnson, W. C. *Proteins*, 7, 205–214 (1990).

Kappler, J. W., Staerz, U., White, J. and Marrack, P. C. *Nature*, 332, 35–40 (1988).

Kyte et al., *J. Mol. Biol.* 157:105–132 (1982)

Lin, A. Y., Devaux, B., Green, A., Sagerström, C. Elliott, J. F. and Davis, M. M. *Science*, 249, 677–679 (1990).

McCafferty et al., *Nature* 348, 552 (1990).

Mariuzza, R. A. and Winter, G. P., *J. Biol. Chem.*, 264, 7310–7316 (1989).

Messing, . . . (1981)

Novotny, J., Tonegawa, S., Saito, H., Kranz, D.M. and Eisen, H. N. *Proc. Natl. Acad. Sci. USA*, 83, 742–746 (1986).

Novotny, J., Gahjn, R. K., Smiley, S. T., Hussey, R. E., Luther, M. A., Recry, M. A., Siciliaro, R. F. and Reinher, E. L. (1991) *Proc. Natl Acad. Sci, USA*, 88, 8646–8650.

Offner, H., Hashim, G. A., Vandenbark, A. A. *Science*, 251, 430–432 (1991).

Rüther, U., Koenen, M., Otto, K. and Müller-Hill, B. *Nucl. Acids Res.*, 9, 4087–4098 (1981).

Saiki, R. K., Gelfand, D. H., Stoffel, S., Scharf, S. J., Higuchi, R., Horn, G. T., Mullis, K. V. and Erlich, H. A. *Science* 239, 487–491 (1988).

Sambrook, J., Fritsch, E. F. and Maniatis, T. in Molecular Cloning; a Laboratory Manual, Cold Spring Harbor Press, 1989.

Sleckman, B. P., Peterson, A., Jones, W. K., Foran, J. A., Greenstein, J. L., Seed, B. and Burakoff, S. J. *Nature*, 328, 351–353 (1987).

Skerra, A. and Plückthun, A. *Science*, 240, 1038–1041 (1988).

Takagi, H., Morinaga, Y., Tsuchiya, M., Ikemura, H. and Inouye, M. *Bio/technol.*, 6, 948–950 (1988).

Towbin, H., Stachelin, T. and Gordon, J. (1979) *Proc. Natl. Acad. Sci.*, 76, 4350–4354.

U.S. Pat. No. 4,554,101, Hoppe, T. P., Nov. 19, 1985.

Vandenbark, A. A., Hashim, G. and Offner, H. *Nature*, 331, 541–544 (1989).

Viera, J. and Messing, J. in 'Methods in Enzymology', (eds. R. Wu and L. Grossman, Academic Press, New York), 153, 3–11 (1987).

Ward, E. S., Gussow, D., Griffiths, A. D., Jones, P. T. and Winter, G. *Nature*, 341, 544–546 (1989).

Whitlow, M. and Filpula, D., in Mehods: A Companion to Methods in Enzymology, Vol. 2, No. 2, p. 97–105 (1991)

Wraith, D. C., Smilek, D. E., Mitchell, D. J., Steinman, L. and McDevitt, H. O. *Cell*, 59, 247–255 (1989).

---

What is claimed is:

1. A cloning vector which expresses and secretes a soluble $V_\alpha$ or $V_\beta$ T-cell receptor variable domain in a gram-negative cell, said secretion being into the bacterial periplasm or into a culture medium, said vector comprising the following elements in the 5' to 3' direction, said elements which are operatively linked:

(a) an inducible promoter DNA sequence;
(b) a leader sequence; and
(c) a DNA sequence encoding a $V_\alpha$ or $V_\beta$ T-cell receptor variable domain.

2. The cloning vector of claim 1 further comprising a DNA sequence encoding a tag sequence, said tag sequence positioned 3' to the DNA encoding said T-cell receptor variable domain.

3. The cloning vector of claim 1 wherein the DNA encodes $V_\alpha$ T-cell receptor variable domain and $V_\beta$ T-cell receptor variable domain.

4. The cloning vector of claim 3 wherein the DNA sequence encoding the $V_\alpha$ T-cell receptor variable domain is 5' to the DNA sequence encoding the $V_\beta$ T-cell receptor variable domain.

5. The cloning vector of claim 2 wherein the tag is myc or his.

6. A gram-negative bacterium transformed by the cloning vector of claim 1.

7. The bacterium of claim 6, identified as *E. coli, S. marcescens,* or *S. typhimurium.*

8. The gram-negative bacterium of claim 7 further characterized as *E. coli* BMH71-18.

9. A method for expressing and secreting a T-cell receptor variable domain in a gram-negative bacterium, comprising the steps:
   a) culturing a gram-negative bacterium transformed with a vector, said vector comprising the following elements in the 5' to 3' direction, said elements which are operatively linked:
      i) an inducible promoter DNA sequence;
      ii) a leader sequence; and
      iii) a DNA sequence encoding a $V_\alpha$ or $V_\beta$ T-cell receptor variable domain; and
   b) inducing said promoter;
      to produce a T-cell receptor variable domain.

10. The method of claim 9 wherein the T-cell receptor variable domain is $V_\alpha$, $V_\beta$, $V_\gamma$, $V_\delta$ single chain $V_\alpha V_\beta$, $scV_\beta V_\alpha$, $scV_\gamma V_\delta$, or $scV_\delta V_\gamma$.

11. The method of claim 9 wherein the gram-negative bacterium is *Escherichia coli, Serratia marcescens*, or *Salmonella typhimurium*.

12. The method of claim 9 wherein the inducing is in a culture medium at about 25° C.

13. The method of claim 9 wherein isolating comprises obtaining TCR protein directly from culture medium supernatant.

14. The method of claim 9 wherein isolating comprises an osmotic shock step.

15. The method of claim 9 further comprising purifying the T-cell receptor domain by affinity metallic resin chromatography.

16. The method of claim 15 wherein the metallic resin is $Ni^{2+}$ NTA.

17. A recombinant T-cell receptor single chain variable domain α,β heterodimer produced by the method of claim 9.

18. The method of claim 9, further comprising isolating the T-cell receptor variable domain so produced.

19. The method of claim 9 wherein the leader sequence is the pelB, ompA or phoA leader sequence.

20. The method of claim 9 wherein the leader sequence is the pelB sequence.

21. The method of claim 9 wherein said inducible promoter is the lacZ promoter and the inducer is isopropylthiogalactopyranoside.

22. The method of claim 10 wherein isolating comprises obtaining the TCR protein from the periplasmic space.

23. The method of claim 21, wherein said inducing comprises the addition of about 0.1 to 1 mM of isopropylthiogalactopyranoside.

24. A method for expressing and secreting a T-cell receptor variable domain in a gram-negative bacterium, comprising the steps:
   a) culturing a gram-negative bacterium transformed with a vector, said vector comprising the following elements in the 5' to 3' direction, said elements which are operatively linked:
      i) a lacZ inducible promoter DNA sequence;
      ii) a leader sequence selected from the group consisting of pelB, ompA and phoA; and
      iii) a DNA sequence encoding at least one of a $V_\alpha$ or $V_\beta$ T-cell receptor variable domain; and
   b) adding about 0.1 to 1 mM of isopropylthiogalactopyranoside;
      to produce a T-cell receptor variable domain.

25. The method of claim 24, wherein said secreted T-cell receptor variable domain has a high proportion of β-sheet structure as indicated by circular dichroism spectra.

26. The method of claim 9, wherein said vector is further defined as comprising a tag sequence, said tag sequence positioned 3' to the DNA encoding said T-cell receptor variable domain.

* * * * *

UNITED STATES PATENT AND TRADEMARK OFFICE
CERTIFICATE OF CORRECTION

| | | |
|---|---|---|
| PATENT NO. | : 6,399,368 B1 | |
| APPLICATION NO. | : 08/353940 | |
| DATED | : June 4, 2002 | |
| INVENTOR(S) | : Ward | |

It is certified that error appears in the above-identified patent and that said Letters Patent is hereby corrected as shown below:

The drawing sheet, consisting of Figs. 1-12, should be deleted to be replaced with drawing sheet, consisting of Figs. 1-11B, as Shown on the attached page.

Signed and Sealed this

Twenty-fourth Day of October, 2006

JON W. DUDAS
*Director of the United States Patent and Trademark Office*

```
1 /   1                                    31 /  11
GAC TCA GTG ACT CAG ACG GAA GGT CAA GTG GCC CTC TCA GAA GAG GAC TTT CTT ACG ATA
asp ser val thr gln thr glu gly gln val ala leu ser glu glu asp phe leu thr ile
 61 /  21                                    91 /  31
CAC TGC AAC TAC TCA GCC TCA GGG TAC CCA CAG GCT CTG TTC TGG TAT GTG CAG TAT CCC GGA
his cys asn tyr ser ala ser gly tyr pro gln ala leu phe trp tyr val gln tyr pro gly
121 /  41                                   151 /  51
GAA GGG CCA CAG TTC CTC TTT AGA GCC TCA AGG GAC AAA GAG AAA GGA AGC AGC AGA GGG
glu gly pro gln phe leu phe arg ala ser arg asp lys glu lys gly ser ser arg gly
181 /  61                                   211 /  71
TTT GAA GCC ACA TAC AAT AAA GAA GCC ACC TCC TTC CAC TTG CAG AAA GCC TCA GTG CAA
phe glu ala thr tyr asn lys glu ala thr ser phe his leu gln lys ala ser val gln
241 /  81                                   271 /  91
GAG TCA GAC TCG GCT GTG TAC TAC TGC GCT AGT CTG GAA AAC TAT GGA AAT GAG AAA ATA
glu ser asp ser ala val tyr tyr cys ala ser leu glu asn tyr gly asn glu lys ile
301 / 101                                   331 / 111
ACT TTT GGG GCT GGA ACC AAA CTC ACC ATT AAA CCG GTC ACC CAT CAC CAT CAC CAT CAC
thr phe gly ala gly thr lys leu thr ile lys pro val thr his his his his his his
361 / 121
TAA
OCH
```

FIG. 5

```
  1   /   1
GAG GCT GCA GTC ACC CAA AGC CCA AGA AAC CCA AGA GTA ACA GGA AAG GTG ACA
glu ala ala val thr gln ser pro arg asn         val thr gly gly lys val thr
 61  /  21                                              31  /  11
TTG AGC TGT AAT CAG ACT AAT AAC CAC AAC ATG TAC TGG CAG GAC ACG GGG
leu ser cys asn gln thr asn asn his asn met tyr trp arg gln asp thr gly
121  /  41                                              91  /  31
CAT GGG CTG AGG CTG ATC CAT TAT TCA TAT GGT GCT GGC AGC ACT GAG AAA GGA GAT ATC
his gly leu arg leu ile his tyr ser tyr gly ala gly ser thr glu lys gly asp ile
181  /  61                                             151  /  51
CCT GAT GGA TAC AAG GCC TCC AGA CCA AGC CAA GAG AAC TTC TCC CTC ATT CTG GAG TTG
pro asp gly tyr lys ala ser arg pro ser gln glu asn phe ser leu ile leu glu leu
241  /  81                                             211  /  71
GCT ACC CCC TCT CAG ACA TCA GTG TAC TTC TGT GCC AGC GGT GAT GCG TCG GGA GCA GAA
ala thr pro ser gln thr ser val tyr phe cys ala ser gly asp ala ser gly ala glu
301  /  101                                            271  /  91
ACG CTG TAT TTT GGC TCA GGA ACC AGA CTG ACT GTT CTG ACC CAT CAC CAT CAC CAT
thr leu tyr phe gly ser gly thr arg leu thr val leu thr his his his his his
361  /  121                                            331  /  111
CAC TAA
his OCH
```

FIG. 6

```
  1 /   1                                                      31 /  11
GAC TCA GTG ACT CAG ACG GAA GGT CAA GTG GCC CTC TCA GAA GAG GAC TTT CTT ACG ATA
asp ser val thr gln thr glu gly gln val ala leu ser glu glu asp phe leu thr ile
 61 /  21                                                      91 /  31
CAC TGC AAC TAC TCA GCC TCA GGG TAC CCA GCT CTG TTC TGG TAT GTG CAG TAT CCC GGA
his cys asn tyr ser ala ser gly tyr pro ala leu phe trp tyr val gln tyr pro gly
121 /  41                                                     151 /  51
GAA GGG CCA CAG TTC CTC TTT AGA GCC TCA AGG GAC AAA GAG AAA GGA AGC AGC AGA GGG
glu gly pro gln phe leu phe arg ala ser arg asp lys glu lys gly ser ser arg gly
181 /  61                                                     211 /  71
TTT GAA GCC ACA TAC AAT AAA GAA GCC ACC TCC TTC CAC TTG CAG AAA GCC TCA GTG CAA
phe glu ala thr tyr asn lys glu ala thr ser phe his leu gln lys ala ser val gln
241 /  81                                                     271 /  91
GAG TCA GAC TCG GCT GTG TAC TAC TGC GCT CTG AGT GAA AAC TAT GGA AAT GAG AAA ATA
glu ser asp ser ala val tyr tyr cys ala leu ser glu asn tyr gly asn glu lys ile
301 / 101                                                     331 / 111
ACT TTT GGG GCT GGA ACC AAA CTC ACC ATT AAA CCG GTC ACC GGT GGA GGC GGT TCA GGC
thr phe gly ala gly thr lys leu thr ile lys pro val thr gly gly gly gly ser gly
361 / 121                                                     391 / 131
GGA GGT GGC TCT GGC GGT GGC GGA TCG GAG GCT GCA GTC ACC CAA AGC CCA AGA AAC AAG
gly gly gly ser gly gly gly gly ser glu ala ala val thr gln ser pro arg asn lys
```

FIG. 7A

```
421 /  141
GTG GCA GTA ACA GGA GGA AAG GTG ACA TTG AGC TGT AAT CAG ACT AAT AAC CAC AAC AAC
val ala val thr gly gly lys val thr leu ser cys asn gln thr asn asn his asn asn
481 /  161                                            451 /  151
ATG TAC TGG TAT CGG CAG GAC ACG GGG CAT GGG CTG ATC CAT TAT TCA TAT GGT
met tyr trp tyr arg gln asp thr gly his gly leu ile his tyr ser tyr gly
541 /  181                                            511 /  171
GCT GGC AGC ACT GAG AAA GGA GAT ATC CCT GAT GGA TAC AAG GCC TCC AGA CCA AGC CAA
ala gly ser thr glu lys gly asp ile pro asp gly tyr lys ala ser arg pro ser gln
601 /  201                                            571 /  191
GAG AAC TTC TCC CTC ATT CTG GAG TTG GCT ACC CCC TCT CAG ACA TCA GTG TAC TTC TGT
glu asn phe ser leu ile leu glu leu ala thr pro ser gln thr ser val tyr phe cys
661 /  221                                            631 /  211
GCC AGC GGT GAT GCG TCG GGA GCA GAA ACG CTG TAT TTT GGC TCA GGA ACC AGA CTG ACT
ala ser gly asp ala ser gly ala glu thr leu tyr phe gly ser gly thr arg leu thr
721 /  241                                            691 /  231
GTT CTG GTC ACC CAT CAC CAT CAC CAT CAC TAA
val leu val thr his his his his his his OCH
                                            751 /  251
```

*FIG. 7B*

```
  1 /   1                                                           31 /  11
GAC TCA GTG ACT CAG ACG GAA GGT CAA GTG GCC CTC TCA GAA GAG GAC TTT CTT ACG ATA
asp ser val thr gln thr glu gly gln val ala leu ser glu glu asp phe leu thr ile
 61 /  21                                                           91 /  31
CAC TGC AAC TAC TCA GCC TCA GGG TAC CCA GCT CTG TTC TGG TAT GTG CAG TAT CCC GGA
his cys asn tyr ser ala ser gly tyr pro ala leu phe trp tyr val gln tyr pro gly
121 /  41                                                          151 /  51
GAA GGG CCA CAG TTC CTC TTT AGA GCC TCA AGG GAC AAA GAG AAA GGA AGC AGC AGA GGG
glu gly pro gln phe leu phe arg ala ser arg asp lys glu lys gly ser ser arg gly
181 /  61                                                          211 /  71
TTT GAA GCC ACA TAC AAT AAA GAA GCC ACC TCC TTC CAC TTG CAG AAA ATA TCA GTG CAA
phe glu ala thr tyr asn lys glu ala thr ser phe his leu gln lys ile ser val gln
241 /  81                                                          271 /  91
GAG TCA GAC TCG GCT GTG TAC TAC TGC GCT GTA CTC ACC ATT AGT CTG GAA AAC TAT GGA
glu ser asp ser ala val tyr tyr cys ala val leu thr ile ser leu glu asn tyr gly
301 / 101                                                          331 / 111
ACT TTT GGG GCT GGA ACC AAA CTC ACC ATT AAA CCG GGT GGA GGC GGT TCA GGC GGA GGT
thr phe gly ala gly thr lys leu thr ile lys pro gly gly gly gly ser gly gly gly
361 / 121                                                          391 / 131
GGA TCC GGC GGT GGC GGA TCG GAG GCT GCA GTC ACC CAA AGC CCA AGA AAC AAG GTG GCA
gly ser gly gly gly gly ser glu ala ala val thr gln ser pro arg asn lys val ala
```

FIG. 9A

```
421  /          141
GTA ACA GGA AAG GTG ACA TTG AGC TGT AAT CAG ACT AAT AAC CAC AAC ATG TAC
val thr gly gly lys val thr leu ser cys asn gln thr asn asn his asn met tyr
481  /          161                         511  /          171
TGG TAT CGG CAG GAC ACG GGG CAT GGG CTG AGG ATC CAT TAT TCA TAT GGT GCT GGC
trp tyr arg gln asp thr gly his gly leu arg ile his tyr ser tyr gly ala gly
541  /          181                         571  /          191
AGC ACT GAG AAA GGA GAT ATC CCT GAT GGA TAC AAG GCC TCC AGA CCA AGC CAA GAG AAC
ser thr glu lys gly asp ile pro asp gly tyr lys ala ser arg pro ser gln glu asn
601  /          201                         631  /          211
TTC TCC CTC ATT CTG GAG TTG GCT ACC CCC TCT CAG ACA TCA GTG TAC TTC TGT GCC AGC
phe ser leu ile leu glu leu ala thr pro ser gln thr ser val tyr phe cys ala ser
661  /          221                         691  /          231
GGT GAT GCG TCG GGA GCA GAA ACG CTG TAT TTT GGC TCA GGA ACC AGA CTG ACT GTT CTG
gly asp ala ser gly ala glu thr leu tyr phe gly ser gly thr arg leu thr val leu
721  /          241
GTC ACC CAT CAC CAT CAC CAT CAC TAA
val thr his his his his his his OCH
```

FIG. 9B